US012473592B2

(12) United States Patent
Choudhury et al.

(10) Patent No.: US 12,473,592 B2
(45) Date of Patent: Nov. 18, 2025

(54) METHOD FOR THE DETECTION AND QUANTIFICATION OF GENETIC ALTERATIONS

(71) Applicant: Lucence Life Sciences Pte. Ltd., Singapore (SG)

(72) Inventors: Yukti Choudhury, Singapore (SG); Hao Chen, Singapore (SG); Min-Han Tan, Singapore (SG)

(73) Assignee: LUCENCE LIFE SCIENCES PTE. LTD., Singapore (SG)

(*) Notice: Subject to any disclaimer, the term of this patent is extended or adjusted under 35 U.S.C. 154(b) by 1107 days.

(21) Appl. No.: 17/182,615

(22) Filed: Feb. 23, 2021

(65) Prior Publication Data

US 2021/0180125 A1 Jun. 17, 2021

Related U.S. Application Data

(63) Continuation of application No. 17/253,857, filed as application No. PCT/SG2019/050317 on Jun. 25, 2019, now abandoned.

(30) Foreign Application Priority Data

Jun. 25, 2018 (SG) .......................... 10201805450Y

(51) Int. Cl.
*C12Q 1/6869* (2018.01)
*C12Q 1/6876* (2018.01)

(52) U.S. Cl.
CPC ......... *C12Q 1/6869* (2013.01); *C12Q 1/6876* (2013.01); *C12Q 2600/156* (2013.01)

(58) Field of Classification Search
None
See application file for complete search history.

(56) References Cited

FOREIGN PATENT DOCUMENTS

| | | | |
|---|---|---|---|
| WO | 2011019964 | A1 | 2/2011 |
| WO | 2014093330 | A1 | 6/2014 |
| WO | 2015039006 | A1 | 3/2015 |
| WO | 2015200541 | A1 | 12/2015 |
| WO | 2016081798 | A1 | 5/2016 |
| WO | 2018111835 | A1 | 6/2018 |

OTHER PUBLICATIONS

International Search Report in reference to co-pending Singapore Patent Application No. PCT/SG2019/050317 filed Jun. 25, 2019.
Written Opinion in reference to co-pending Singapore Patent Application No. PCT/SG2019/050317 filed Jun. 25, 2019.
Hu, et al., "Detecting DNA Double-Stranded Breaks in Mammalian Genomes by Linear Amplification-mediated High-Throughput Genome-wide Translocation Sequencing (LAM-HTGTS)", Nat. Protoc., vol. 5, pp. 853-871, May 2016.
Illumina, "TruSeq DNA Library Prep Kits", Data Sheet: Sequencing, pp. 1-3, Nov. 17, 2014.
Brandariz-Fontes, C. et al. "Effect of the enzyme and PCR conditions on the quality of high-throughput DNA sequencing results" Scientific Reports, Jan. 27, 2015, pp. 1-5, 5:8056, DOI: 10.1038/srep08056.
Pelechano, V. et al. "Extensive transcriptional heterogeneity revealed by isoform profiling" Nature, Apr. 24, 2013, pp. 127-131, vol. 497, DOI: 10.1038/nature12121.
U.S. Office Action dated Aug. 17, 2023 pertaining to U.S. Appl. No. 17/977,551, filed Oct. 31, 2022, pp. 1-17.
European Search Reporting in reference to co-pending European Application No. 19825310.6 filed Jun. 25, 2019.
Wang, et al., "Targeted sequencing of both DNA strands barcoded and captured individually by RNA probes to identify genome-wide ultra-rare mutations", Science Reports, vol. 7, pp. 1-14, 2017.
Kennedy, et al., "Detecting ultralow-frequency mutations by Duplex Sequencing", Nat. Protoc., vol. 9, No. 11, pp. 2586-2606, Nov. 2014.
Singapore Office Action dated Dec. 20, 2023.
TruSeq® DNA Library Prep Kits Data Sheet, Illumina, Inc. (Nov. 17, 2014).
Hu, et al., "Detecting DNA Double-Stranded Breaks in Mammalian Genomes by Linear Amplification-mediated High-Throughput Genome-wide Translocation Sequencing (LAM-HTGTS)", Nat. Protoc., vol. 11, No. 5, pp. 853-871, May 2016.
Wang, et al., "Targeted sequencing of both DNA strands barcoded and captured individually by RNA probes to identify genome-wide ultra-rare mutations", Scientific Reports, vol. 7, pp. 1-14, 2017.
Ciuffi, A. et al. "Identification of HIV integration sites in infected host genomic DNA" Methods, 2011, pp. 39-46, vol. 53, doi: 10.1016/j.ymeth.2010.04.004.
U.S. Office Action dated Dec. 19, 2023 pertaining to U.S. Appl. No. 17/977,551, filed Oct. 31, 2022, pp. 1-8.

*Primary Examiner* — Nancy J Leith
*Assistant Examiner* — Jessica D Parisi
(74) *Attorney, Agent, or Firm* — DINSMORE & SHOHL LLP

(57) ABSTRACT

Disclosed is a method of simultaneously capturing and identifying distinct targets within a DNA sample, wherein the distinct targets comprise a defined target region and an undefined target region, wherein the undefined target region comprises a structural variation or rearrangement or fusion. Also disclosed is a kit comprising the reagents for use in the methods as described herein.

30 Claims, 27 Drawing Sheets

Specification includes a Sequence Listing.

| | 0% VAF | | 0.1% VAF | | 1% VAF | | 5% VAF | |
|---|---|---|---|---|---|---|---|---|
| Variant | Expected | Observed | Expected | Observed | Expected | Observed | Expected | Observed |
| EGFR E746_A750delELRA | 0.00 | 0.00 | 0.10 | 0.06 | 1.00 | 1.79 | 5.00 | 6.50 |
| EGFR L858R | 0.00 | 0.00 | 0.10 | 0.12 | 1.00 | 0.62 | 5.00 | 6.07 |
| EGFR T790M | 0.00 | 0.00 | 0.10 | 0.04 | 1.00 | 0.17 | 5.00 | 3.21 |
| EGFR V769_D770insASV | 0.00 | 0.00 | 0.10 | 0.14 | 1.00 | 1.38 | 5.00 | 7.20 |
| KRAS G12D | 0.00 | 0.00 | 0.10 | 0.06 | 1.00 | 0.87 | 5.00 | 4.38 |
| NRAS A59T | 0.00 | 0.00 | 0.10 | 0.05 | 1.00 | 0.53 | 5.00 | 6.27 |
| NRAS Q61K | 0.00 | 0.00 | 0.10 | 0.16 | 1.00 | 1.23 | 5.00 | 8.14 |
| PIK3CA E545K | 0.00 | 0.00 | 0.10 | 0.12 | 1.00 | 2.15 | 5.00 | 7.26 |
| Average | 0.00 | 0.00 | 0.10 | 0.09 | 1.00 | 1.09 | 5.00 | 6.13 |
| SD | 0.00 | 0.00 | 0.00 | 0.05 | 0.00 | 0.67 | 0.00 | 1.61 |

Figure 4a

| | Variant allele frequency | 0.10% | | 1% | | 5% | |
|---|---|---|---|---|---|---|---|
| | | Sensitivity | Specificity | Sensitivity | Specificity | Sensitivity | Specificity |
| Mutation Class | SNVs | >67% | >99% | >99% | >99% | >99% | >99% |
| | INDELs | >99% | >99% | >99% | >99% | >99% | >99% |

Figure 4c

5' ACACGACGCTCTTCCGATCTNNNNNNNNNNNNGGTGACCCTTGTCTCTGTGTTCgtcgaacacctcggagaatgtgggtcacctcttcAGATCGGAAGAGCACACGTC
3' CCACTGGGAACAGAGACACAAGcagcttgtggagcctcttacacccagtggagaagTCTAGCCTTCTCGTGTGCAG

Figure 8a

5' ACACGACGCTCTTCCGATCTNNNNNNNNNNNNGGTGACCCTTGTCTCTGTGTTCgtcgaacacctcggagaatgtgggtcacctcttc~gene-specific~AGATCGGAAGAGCACACGTC
TGTGCTGCGAGAAGGCTAGANNNNNNNNNNNNCCACTGGGAACAGAGACACAAGcagcttgtggagcctcttacacccagtggagaag~~~~~~~~~~~~~~~ TCTAGCCTTCTCGTGTGCAG

Figure 8b

5' AATGATACGGCGACCACCGAGATCTACACTCTTTCCCTACACGACGCTCTTCCGATCTNNNNNNNNNNNNGGTGACCCTTGTCTCTGTGTTCgtcgaacacc
tcggagaatgtgggtcacctcttcAGATCGGAAGAGCACACGTCTGAACTCCAGTCACCGTGATATCTCGTATGCCGTCTTCTGCTTG 3'

Figure 9

Table 2. Mutation detection and frequency in 16 clinical samples (plasma) tested by the method of the present invention and by quantitative PCR.

| | Quantitative PCR | | The method of the present invention | | | | | | |
|---|---|---|---|---|---|---|---|---|---|
| Sample | Mutation reported by AS-PCR | Frequency reported by AS-PCR | Amount of DNA used for library preparation (ng) | Theoretical DNA copies available for conversion | Variant identified by Hallmark | Total consensus read depth | Variant consensus read depth | Frequency | Concordance |
| 1 | EGFR L858R | 1.10% | 4.65 | 1534 | EGFR L858R | 243 | 6 | 2.47% | Yes |
| 2 | EGFR L858R | 3.95% | 9.02 | 2977 | EGFR L858R | 288.00 | 7 | 2.43% | Yes |
| | EGFR T790M | 3.15% | | | EGFR T790M | 284 | 10 | 3.52% | Yes |
| 3 | EGFR E746_A750del | >5% | 20.00 | 6600 | EGFR E746_A750del (c.2235_2249del) | 1936 | 1464 | 75.62% | Yes |
| | EGFR T790M | >5% | | | EGFR T790M | 2313 | 150 | 6.49% | Yes |
| 4 | EGFR L858R | 1-5% | 5.96 | 1967 | L858R | 478 | 9 | 1.88% | Yes |
| 5 | EGFR T790M | 0.10% | 7.99 | 2637 | T790M | 362 | 0 | ND | No |
| | | | | | L858R | 730 | 2 | 0.27% | Yes |
| 6 | EGFR E746_A750del | 1.07% | 12.08 | 3988 | EGFR E746_A750del | 876 | 22 | 2.51% | Yes |
| 7 | EGFR E746_A750del | >5% | 13.40 | 4422 | EGFR E746_A750del | 800 | 42 | 5.25% | Yes |
| 8 | E746_A750del | 1.06% | 15.50 | 5114 | EGFR E746_A750del | 796 | 10 | 1.26% | Yes |
| 9 | E746_A750del | 0.27% | 13.46 | 4442 | EGFR E746_A750del | 744 | 4 | 0.54% | Yes |

FIG. 15a

Table 2, Continued

| | | | | | | | | | |
|---|---|---|---|---|---|---|---|---|---|
| 10 | unspecified exon 19 | >5% | 20.00 | 6600 | EGFR c.2236_2250del | 1842 | 188 | 10.21% | Yes |
| 11 | unspecified exon 19 | 3.20% | 18.42 | 6079 | EGFR c.2236_2250del | 1672 | 106 | 6.34% | Yes |
| | | | | | KRAS G12D | 2000 | 6 | 0.30% | Not tested by qPCR |
| 12 | EGFR L747_P753delinsS | >5% | 10.98 | 3623 | EGFR L747_P753delinsS | 595 | 61 | 10.25% | Yes |
| | EGFR T790M | 0.90% | | | T790M | 485 | 8 | 1.65% | Yes |
| 13 | none | | 100.00 | 33000 | none | | | | Yes |
| 14 | EGFR L858R | 2.10% | 50.00 | 16500 | EGFR L858R | 265 | 2 | 0.75% | Yes |
| 15 | EGFR E746_A750del | >5% | 30.00 | 9900 | E746_A750delELRA | 653 | 114 | 17.46% | Yes |
| | | | | | EGFR T790M | 779 | 6 | 0.77% | Yes |
| | | | | | PIK3CA E545A | 4576 | 58 | 1.27% | Not tested by qPCR |
| 16 | KRAS G12D | >5% | 10.00 | 3300 | KRAS G12D | 668 | 260 | 38.92% | Yes |
| | | | | | PIK3CA Q546R | 2161 | 1696 | 78.48% | Not tested by qPCR |

FIG. 15b

Table 3. Detection of Epstein Barr Virus (EBV) microbial DNA targets BamHI-W and EBNA1, in clinical samples (plasma) by the method of the present invention and qPCR.

| | Quantitative PCR | | The method of the present invention | | | | | | | | | | | |
|---|---|---|---|---|---|---|---|---|---|---|---|---|---|---|
| Sample | EBV BamHI-W | EBV IU/mL | Amount of DNA (ng) | Vol. of input DNA (ul) | Number of total reads | Number of BamH1-W1 (consensus paired read mean depth) | Number of BamH1-W-2 | EBNA -1-1 | EBNA-1-2 | Mutations | Total read depth | Variant read depth | Frequency | Concordance |
| 17 | 21434 copies/ mL | 2146 IU/mL | 11.25 | 26.4 | 1139942 | 451 | 151 | 16 | 0 | KIT c.1621A>C p.Met541Leu | 57 | 26 | 45.61 | Yes |
| 18 | 1150 copies/ mL | 115 IU/mL | 50 | 5.8 | 3628698 | 0 | 0 | 0 | 0 | VHL c.556G>A p.Glu186Lys | 1393 | 8 | 0.57 | |
| | | | | | | | | | | APC c.4351G>A p.Glu1451Lys | 3544 | 5 | | |
| | | | | | | | | | | APC c.848G>A p.Arg283Gln | 692 | 3 | 0.43 | |
| | | | | | | | | | | PTEN c.961G>A p.Ala321Thr | 590 | 4 | 0.68 | No |

FIG. 16a

Table 3, Continued

| | | | | | | | | | | | | | | |
|---|---|---|---|---|---|---|---|---|---|---|---|---|---|---|
| 19 | 4715 copies/ mL | 472 IU/mL | 9.19 | 26.4 | 853478 | 72 | 38 | 8 | 0 | PIK3CA c.929G>A p.Arg310His | 264 | 4 | 1.52 | |
| | | | | | | | | | | PTEN c.511C>G p.Leu171Val | 362 | 182 | 50.28 | Yes |
| 20 | 4772 copies/ mL | 478 IU/mL | 50 | 24.5 | 4592289 | 104 | 46 | 12 | 0 | APC c.4435G>A p.Val1479Ile | 556 | 3 | 0.54 | Yes |
| 21 | 81371 copies/ mL | 8147 IU/mL | 35 | 21.4 | 3830404 | 1776 | 984 | 146 | 0 | | | | | Yes |
| 22 | 2169 copies/ mL | 217 IU/mL | 6.54 | 26.4 | 563957 | 344 | 128 | 0 | 0 | | | | | Yes |
| 23 | 4606 copies/ mL | 461 IU/mL | 7.66 | 26.4 | 610017 | 272 | 98 | 2 | 0 | | | | | Yes |
| 24 | >12,500,000 copies/ mL | >1,251,539 IU/mL | 100 | 7.7 | 1139394 | 7335.824 | 1261.985 | 55 | 5 | TP53 c.488A>G p.Tyr163Cys | 827 | 6 | | Yes |
| 25 | 7,928,069 copies/ mL | 793,783 IU/mL | 75 | 21.4 | 5708489 | 330336 | 87071 | 19793 | 214 | APC c.647G>A p.Arg216Gln | 3653 | 5 | 0.14 | |

FIG. 16b

Table 3, Continued

| | | | | | | | | | | | | | | |
|---|---|---|---|---|---|---|---|---|---|---|---|---|---|---|
| | | | | | | | | | | TP53 c.488A>G p.Tyr163Cys | 1907 | 7 | 0.37 | |
| | | | | | | | | | | ERBB2 c.308G>A p.Arg103Gln | 5450 | 8 | 0.15 | |
| | | | | | | | | | | MED12 c.127C>A p.Gln43Lys | 2102 | 2 | 0.10 | Yes |
| 26 | >12,500,000 copies/mL | >1,251,539 IU/mL | 100 | 7.7 | 5776267 | 187656 | 41864 | 3160 | 135 | TP53 c.488A>G p.Tyr163Cys | 1918 | 6 | 0.31 | |
| | | | | | | | | | | MED12 c.127C>A p.Gln43Lys | 3085 | 8 | 0.26 | |
| | | | | | | | | | | ERBB2 c.308G>A p.Arg103Gln | 8419 | 6 | 0.07 | Yes |
| 27 | 4,676,723 copies/mL | 468,248 IU/mL | 38 | 21.4 | 4999332 | 214665 | 59188 | 9954 | 314 | TP53 c.488A>G p.Tyr163Cys | 1519 | 16 | 1.05 | |
| | | | | | | | | | | ESR1 c.1436G>A p.Arg479Gln | 27576 | 14 | 0.05 | Yes |

FIG. 16c

Table 3, Continued

| | | | | | | | | | | | | | | |
|---|---|---|---|---|---|---|---|---|---|---|---|---|---|---|
| 28 | >12,500,000 copies/mL | >1,251,539 IU/mL | 100 | 20.3 | 6096667 | 191760 | 51912 | 4096 | 98 | TP53 c.779_781del p.Ser260_Ser261delinsCys | 3038 | 11 | 0.36 | |
| | | | | | | | | | | TP53 c.488A>G p.Tyr163Cys | 1953 | 9 | 0.46 | |
| | | | | | | | | | | APC c.647G>A p.Arg216Gln | 9217 | 10 | 0.11 | |
| | | | | | | | | | | ESR1 c.1436G>A p.Arg479Gln | 27576 | 14 | 0.05 | Yes |
| 29 | negative | | 20 | 21.4 | 3533856 | 0 | 0 | 0 | 0 | none | | | | Yes |
| 30 | 137384 copies/mL | 13755 IU/mL | 12 | 36 | 1235103 | 2110 | 868 | 24 | 16 | MED12 c.115T>G p.Leu39Val | 321 | 4 | 1.25 | Yes |
| 31 | Negative | | 11.04 | 26.4 | 1038667 | 16 | 10 | 0 | 2 | None | | | | No |
| 32 | 348,261 copies/mL | 34,869 IU/mL | 7 | 30 | 618404 | 6541 | 2102 | 90 | 10 | MED12 c.100-4T>G | 16 | 3 | 18.75 | Yes |

FIG. 16d

Table 3, Continued

| | | | | | | | | | | | | | | |
|---|---|---|---|---|---|---|---|---|---|---|---|---|---|---|
| 33 | 4715 copies/ mL | 472 IU/mL | 50 | 26.4 | 4685117 | 2 | 0 | 0 | 0 | None | | | | Yes |
| 34 | 4772 copies/ mL | 478 IU/mL | 50 | 24.5 | 1296750 | 34 | 12 | 2 | 0 | | | | | Yes |
| 35 | 1298 copies/ mL | 130 IU/mL | 45 | 26.4 | 3936664 | 34 | 14 | 2 | 0 | AR c.2062G>A p.Ala688Thr | 272 | 4 | | Yes |

FIG. 16e

METHOD FOR THE DETECTION AND QUANTIFICATION OF GENETIC ALTERATIONS

CROSS-REFERENCE TO RELATED APPLICATIONS

This application is a Continuation of U.S. application Ser. No. 17/253,857, filed Dec. 18, 2020, which claims the benefit of National Stage Entry under 35 U.S.C. § 371 of International Patent Application No. PCT/SG2019/050317, filed 25 Jun. 2019, which claims the benefit of priority of Singapore patent application Ser. No. 10201805450Y, filed 25 Jun. 2018, the contents of which are hereby incorporated by reference in their entireties for all purposes.

SEQUENCE LISTING

A sequence listing in ASCII format having file name Sequence_Listing.txt (9,067 bytes), created on Feb. 23, 201, is incorporated herein by reference.

FIELD OF THE INVENTION

The present invention relates to the measuring or testing processes involving nucleic acid. In particular, the present invention relates to the detection, quantification, and identification of DNA.

BACKGROUND

Detection and quantification of rare genetic events, including low level microbial DNA, is complicated by nature. Typically, high-throughput detection methodologies, which are characterized by an error rate of 0.1-1%, with every 1 of 100 or 1000 bases being called incorrectly due to artifacts introduced during sample preparation and sequencing, are needed to detect and quantify rare genetic events. High-throughput detection methodologies known in the art, however, require repeated sampling or deep sequencing of a large number of molecules, that may not be readily possible due to limitations of sample input amount. To overcome limitations of sample input, the person skilled in the art typically would have to amplify the nucleic acid sequences present in the sample. However, it is generally accepted that amplification methods known in the art are not reliable and do not retain the degree of accuracy demanded for the detection of genomic alterations that occur at extremely low frequencies (i.e. <1%) in the background of otherwise unchanged DNA.

Additionally, conventional methods for simultaneously evaluating point mutations, small INDELs and structural variants make use of the hybridization-based approach capture methods which tend to capture off-target regions besides (or in addition to) sequences targeted by capture probes. These off-target regions consume sequencing capacity which is undesirable from the viewpoint of cost-reduction and simplification of analytical methods. Hybridization methods also take much longer for library preparation and have lower specificity of target capture with off-target regions being captured by the hybridization probes. On the other hand, conventional methods for target capture using forward and reverse primers flanking the target loci, are limited to being able to capture only structural variants with previously known or characterized breakpoints. For the detection of genomic rearrangements with unknown fusion partners, the conventional method (e.g. a pure PCR-based approach) is therefore not applicable. Therefore, there is a need for an alternative method for capturing and identifying distinct targets within a DNA sample. The method should seek to retain specificity of target capture while being able to identify targets of multiple classes.

Thus, the method of the present invention seeks to impart specificity of target capture while not being limited to capturing target regions with previously known sequence changes. The present invention also seeks to provide an alternative method of detecting and/or quantifying genetic alterations that address reliable detection and a system of verification to ensure errors that occur during amplifications are removed from further processing.

SUMMARY

In one aspect, the present invention provides a method of simultaneously capturing and identifying distinct targets within a DNA sample, wherein the distinct targets comprise a defined target region and an undefined target region, wherein the undefined target region comprises structural variations or rearrangement or fusion, comprising the steps of:

a. providing a main mixture comprising a plurality of double stranded DNA fragments A, a plurality of double stranded DNA fragments B, a polymerase, a primer A, and a primer B, wherein:
   - the double stranded DNA fragment A is a double stranded DNA fragment comprising a part of the defined target region;
   - the double stranded DNA fragment B is a double stranded DNA fragment comprising a part of the undefined target region;
   - the primer A comprises, a barcode sequence, and a target-specific sequence A,
     - wherein the target-specific sequence A is an oligonucleotide complementary to a sequence at/close to the 3' end of a single strand of the double stranded DNA fragment A;

and
   - the primer B comprises a separation molecule, a barcode sequence, and a target-specific sequence B,
     - wherein the target-specific sequence B is an oligonucleotide complementary to a sequence within a single strand of the double stranded DNA fragment B, b. denaturing the double stranded DNA fragment A and the double stranded DNA fragment B thereby allowing the primer A to anneal to a single stranded DNA fragment A and the primer B to anneal to the single stranded DNA fragment B;

c. allowing the polymerase to elongate the primer A and the primer B thereby obtaining a double stranded product A and a double stranded product B, wherein:
   - the double stranded product A is a single stranded elongated primer A that is annealed to the single stranded DNA fragment A; and
   - the double stranded product B is a single stranded elongated primer B that is annealed to the single stranded DNA fragment B;

d. adding a bead that binds the separation molecule to the main mixture and allowing the separation molecule in the double stranded product B to bind to the bead thereby forming a double stranded complex B;

e. separating the double stranded product A and the double stranded complex B in the main mixture thereby obtaining a mixture A and a mixture B, wherein:

the mixture A comprises the double stranded product A; and the mixture B comprises the double stranded complex B;

f. adding a primer C to the mixture A, wherein the primer C comprises a target-specific sequence C, wherein the target-specific sequence C is an oligonucleotide complementary to a sequence at/close to the 3' end of the single stranded elongated primer A;

g. denaturing the double stranded product A in the mixture A thereby allowing the primer C to anneal to the single stranded elongated primer A;

h. allowing the polymerase to elongate the primer C thereby obtaining a double stranded product C, wherein the double stranded product C is a single stranded elongated primer C that is annealed to the single stranded elongated primer A;

i. connecting a single nucleotide to the 3' end of the single stranded elongated primer B of the double stranded complex B in the mixture B;

j. adding a double stranded oligonucleotide to the mixture B wherein the double stranded oligonucleotide comprises a nucleotide overhang complementary to the single nucleotide of step i;

k. ligating the double stranded oligonucleotide to double stranded complex B at the 3' end of the single stranded elongated primer B and 5'end of the single stranded DNA fragment B thereby obtaining a double stranded product D;

l. combining the double stranded product C and the double stranded product D;

m. amplifying the double stranded product C and the double stranded product D thereby obtaining a plurality of amplicons;

n. sequencing the plurality of amplicons thereby obtaining a plurality of sequencing result;

o. using the plurality of sequencing results for:

identifying single nucleotide sequence variations, or small insertions, or small deletions, or copy number alteration, or deletions of homopolymeric regions, or polymorphism, or microsatellite instability within the defined target regions, or identifying the structural variations within the undefined target regions, or quantifying the number of distinct targets within the DNA sample.

In one embodiment, the barcode sequence is an oligonucleotide comprising 10 to 16 random nucleotides, or 10 to 15 random nucleotides, or 10 to 13 random nucleotides, or 10 random nucleotides, or 11 random nucleotides, or 12 random nucleotides, or 13 random nucleotides, or 14 random nucleotides, or 15 random nucleotides, or 16 random nucleotides. In another embodiment, the barcode sequence is an oligonucleotide comprising 10 random nucleotides.

In yet another embodiment, the primer A, the primer B, the primer C and/or the double stranded oligonucleotide further comprises an adapter sequence.

In yet another embodiment, the structural variation is selected from the group consisting of deletion, duplication, insertion, inversion, transversion, and translocation.

In yet another embodiment, the sequencing result is further used to detect a point mutation within the undefined target regions.

In yet another embodiment, step o further comprises:

a. grouping the sequencing results wherein the barcodes are identical into a subgroup;

b. comparing the sequencing results within the subgroup thereby determining a consensus sequence;

c. mapping the consensus sequence to a reference sequence; and d. identifying differences between the consensus sequence and the reference sequence.

In yet another embodiment, the length of the target-specific sequence A, the target-specific sequence B, and/or the target-specific sequence C is from 16 nucleotides to 30 nucleotides, or from 19 nucleotides to 29 nucleotides, or from 20 nucleotides to 28 nucleotides, or from 21 nucleotides to 27 nucleotides, or from 22 nucleotides to 26 nucleotides, or 16 nucleotides, or 17 nucleotides, or 18 nucleotides, or 19 nucleotides, or 20 nucleotides, or 21 nucleotides, or 22 nucleotides, or 23 nucleotides, or 24 nucleotides, or 25 nucleotides, or 26 nucleotides, or 27 nucleotides, or 28 nucleotides, or 29 nucleotides, or 30 nucleotides.

In yet another embodiment, the separation molecule is selected from the group consisting of biotin, digoxigenin (DIG), and Fluorescein isothiocyanate (FITC). In yet another embodiment, the separation molecule is biotin.

In yet another embodiment, the bead that binds the separation molecule comprises streptavidin, anti-digoxigenin, or anti-FITC. In yet another embodiment, the bead that binds the separation molecule comprises streptavidin.

In yet another embodiment, the DNA sample is obtained from a subject having and/or suspected of having a disease. In yet another embodiment, the disease is cancer or infectious disease. In yet another embodiment, the cancer is selected from the group consisting of lung cancer, colorectal cancer, breast cancer, pancreatic cancer, prostate cancer, nasopharyngeal cancer, liver cancer, cholangiocarcinoma, esophageal cancer, urothelial cancer, and gastrointestinal cancer. In yet another embodiment, the infectious disease is viral infection and bacterial infection.

In yet another embodiment, the DNA sample is a liquid sample, a tissue sample, or a cell sample. In yet another embodiment, the liquid sample is bodily fluids selected from the group consisting of blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice, and pancreatic juice. In yet another embodiment, the bodily fluid is blood. In yet another embodiment, the tissue sample is a frozen tissue sample or a fixed tissue sample.

In yet another embodiment, the length of the DNA fragment A and/or the DNA fragment B is from 80 base pairs to 220 base pairs, or from 90 base pairs to 210 base pairs, or from 100 base pairs to 200 base pairs, or from 110 base pairs to 190 base pairs, or from 120 base pairs to 180 base pairs, or from 130 base pairs to 170 base pairs, or from 140 base pairs to 160 base pairs, or about 80 base pairs, or about 90 base pairs, or about 100 base pairs, or about 110 base pairs, or about 120 base pairs, or about 130 base pairs, or about 140 base pairs, or about 150 base pairs, or about 160 base pairs, or about 170 base pairs, or about 180 base pairs, or about 190 base pairs, or about 200 base pairs, or about 210 base pairs, or about 220 base pairs. In yet another embodiment, the length of the DNA fragment A and/or the DNA fragment B is about 150 base pairs.

In yet another embodiment, the amount of DNA sample is from 10 ng to 200 ng, or from 20 ng to 190 ng, or from 30 ng to 180 ng, or from 40 ng to 170 ng, or from 50 ng to 160 ng, or from 60 ng to 150 ng, or from 70 ng to 140 ng, or from 80 ng to 130 ng, or from 90 ng to 120 ng, or from 100 ng to 110 ng, or about 10 ng, or about 20 ng, or about 30 ng, or about 40 ng, or about 50 ng, or about 60 ng, or about 70 ng, or about 80 ng, or about 90 ng, or about 100 ng, or about 110 ng, or about 120 ng, or about 130 ng, or about 140 ng, or about 150 ng, or about 160 ng, or about 170 ng, or about 180 ng, or about 190 ng, or about 200 ng. In yet another embodiment, the amount of DNA sample is about 100 ng.

In yet another embodiment, the DNA sample is selected from the group consisting of a eukaryotic DNA sample, a prokaryotic DNA sample, a viral DNA sample, and a mixture thereof. In yet another embodiment, the prokaryotic DNA sample is a bacterial DNA sample.

In yet another embodiment, the eukaryotic DNA sample is selected from the group consisting of a protozoa DNA sample, a fungal DNA sample, an algae DNA sample, a plant DNA sample, and an animal DNA sample. In yet another embodiment, the animal DNA sample is a mammalian DNA sample. In yet another embodiment, the mammalian DNA sample is a human DNA sample. In yet another embodiment, the DNA sample is a cell free DNA or DNA of a lysed cell.

Advantageously, the method described herein allows for simultaneous capture and identification of both defined target regions and undefined target regions within a DNA sample, which increases efficiency of the detection, quantification, and identification of DNA.

Advantageously, the method described herein does not require initial splitting of the sample at the target capture step, and a single sample is used for capturing both the defined target region and the undefined target region. Thus, the copy number of the DNA fragments that can be accessed by both the primer that targets the defined target region (i.e. primer A) and the primer that targets the undefined target region (i.e. primer B) is not reduced. Accordingly, the method achieves high sensitivity and specificity.

Advantageously, the method described herein is able to achieve simultaneous detection of: 1) Viral DNA; 2) Microsatellite instability; 3) Structural rearrangements; 4) SNVs and INDELs from samples ranging from cfDNA from plasma (or cerebrospinal fluid, pleural effusion) or DNA from fixed tissue.

In another aspect, the present invention provides a kit comprising a plurality of primer A as defined herein, a plurality of primer B as defined herein, a plurality of primer C as defined herein, a bead that binds the separation molecule as defined herein, and a double stranded oligonucleotide as defined herein. In yet another embodiment, the kit further comprises a DNA polymerase, a Taq polymerase, a ligase, and a plurality of deoxyribonucleotide triphosphate (dNTPs).

BRIEF DESCRIPTION OF THE DRAWINGS

The invention will be better understood with reference to the detailed description when considered in conjunction with the non-limiting examples and the accompanying drawings, in which.

a. providing a main mixture comprising a plurality of double stranded DNA fragments A, a plurality of double stranded DNA fragments B, a polymerase, a primer A, and a primer B, wherein:
    - the double stranded DNA fragment A is a double stranded DNA fragment comprising a part of the defined region;
    - the double stranded DNA fragment B is a double stranded DNA fragment comprising a part of the undefined region;
    - the primer A comprises, a barcode sequence, and a target-specific sequence A,
        - wherein the target-specific sequence A is an oligonucleotide complementary to a sequence at/close to the 3' end of a single strand of the double stranded DNA fragment A; and
    - the primer B comprises a separation molecule, a barcode sequence, and a target-specific sequence B,
        - wherein the target-specific sequence B is an oligonucleotide complementary to a sequence within a single strand of the double stranded DNA fragment B, b. denaturing the double stranded DNA fragment A and the double stranded DNA fragment B thereby allowing the primer A to anneal to a single stranded DNA fragment A and the primer B to anneal to the a single stranded DNA fragment B.

Figure 1A:
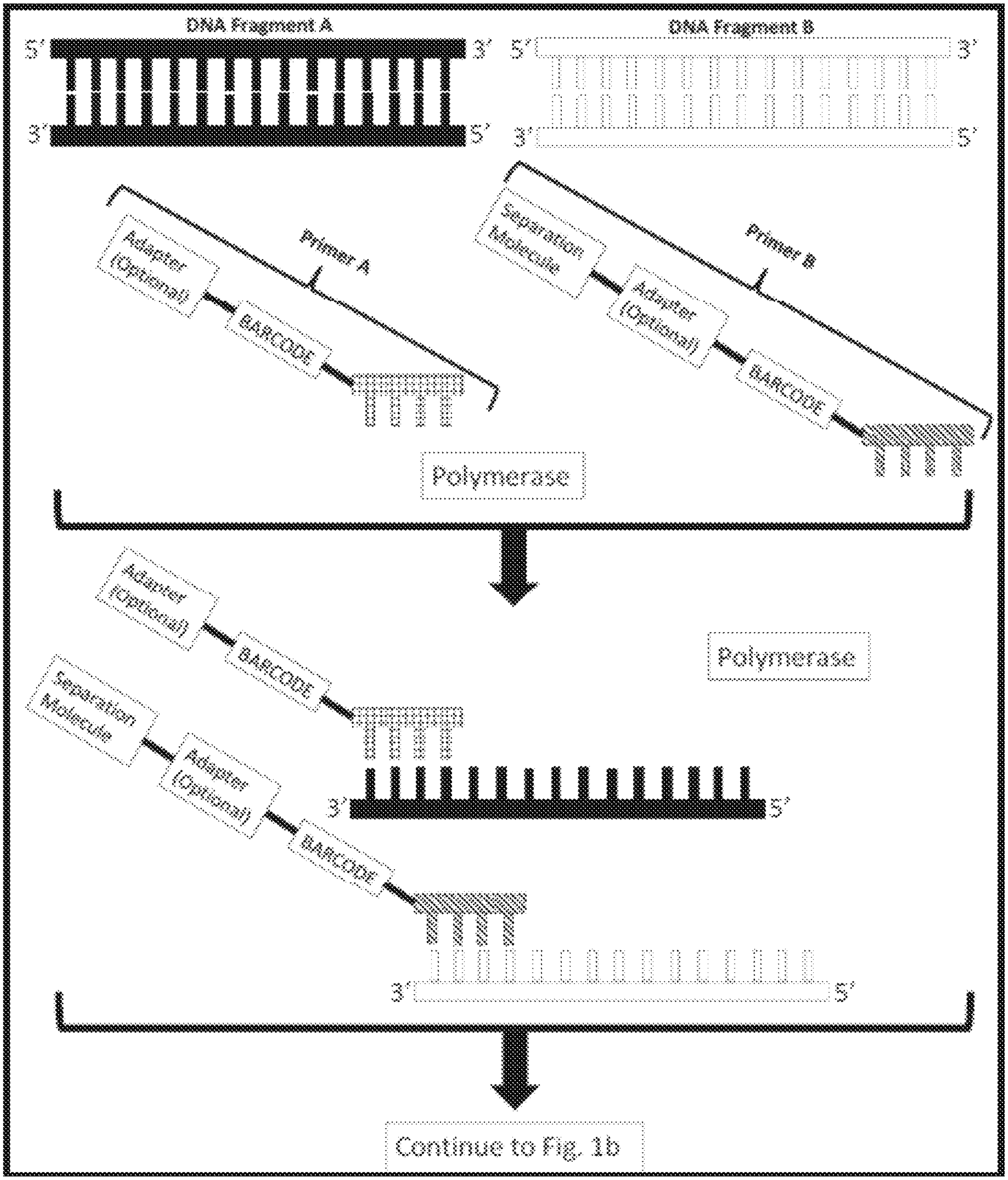
FIG. 1 is a schematic diagram of the method as described herein. That is, FIG. 1*a* describes steps a and b of the method as described herein, which are.
Figure 1B:
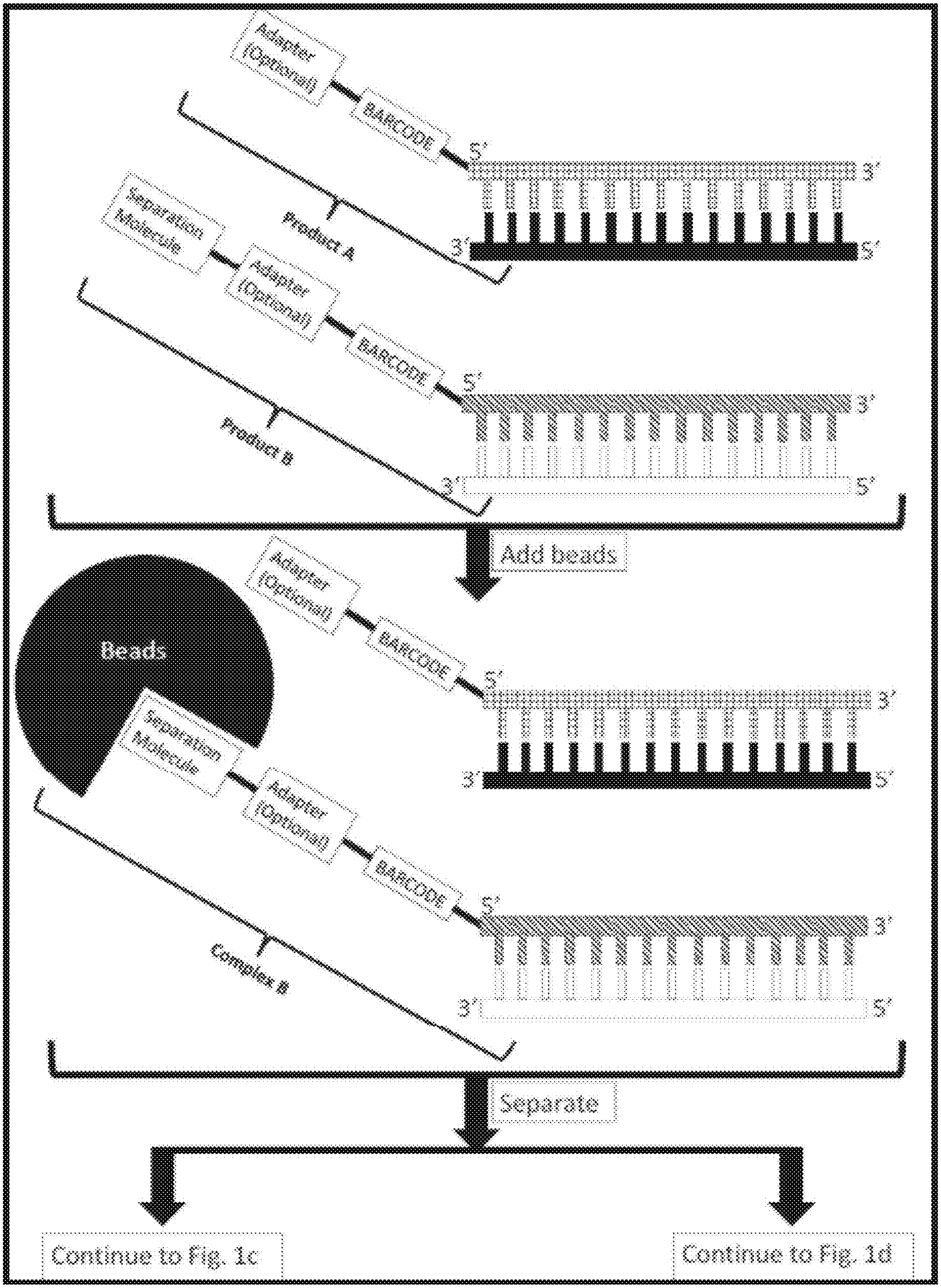

FIG. 1*b* describes steps c to e as follows:

c. allowing the polymerase to elongate the primer A and the primer B thereby obtaining a double stranded product A and a double stranded product B, wherein:
    - the double stranded product A is a single stranded elongated primer A that is annealed to the single stranded DNA fragment A and
    - the double stranded product B is a single stranded elongated primer B that is annealed to the single stranded DNA fragment B;

d. adding a bead that binds the separation molecule to the main mixture and allowing the separation molecule in the double stranded product B to bind to the bead thereby forming a double stranded complex B;

e. separating the double stranded product A and the double stranded complex B in the main mixture thereby obtaining a mixture A and a mixture B, wherein:
    - the mixture A comprises the double stranded product A and
    - the mixture B comprises the double stranded complex B.

Figure 1C:
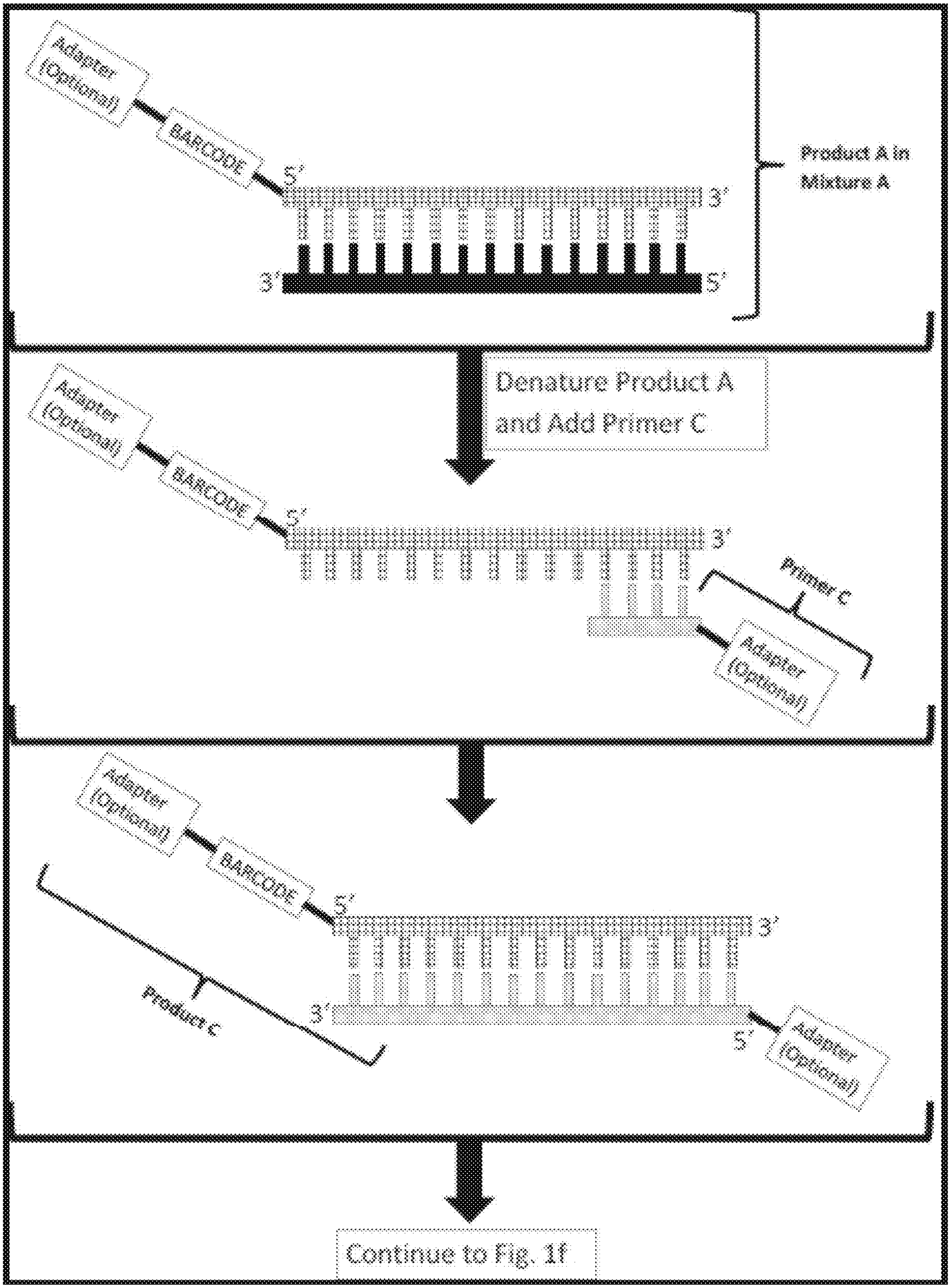

FIG. 1*c* illustrates steps f to h as follows:

f. adding a primer C to the mixture A, wherein the primer C comprises a target-specific sequence C, wherein the target-specific sequence C is an oligonucleotide complementary to a sequence at/close to the 3' end of the single stranded elongated primer A;

g. denaturing the double stranded product A in the mixture A thereby allowing the primer C to anneal to the single stranded elongated primer A;

h. allowing the polymerase to elongate the primer C thereby obtaining a double stranded product C, wherein the double stranded product C is a single stranded elongated primer C that is annealed to the single stranded elongated primer A.

Figure 1D:
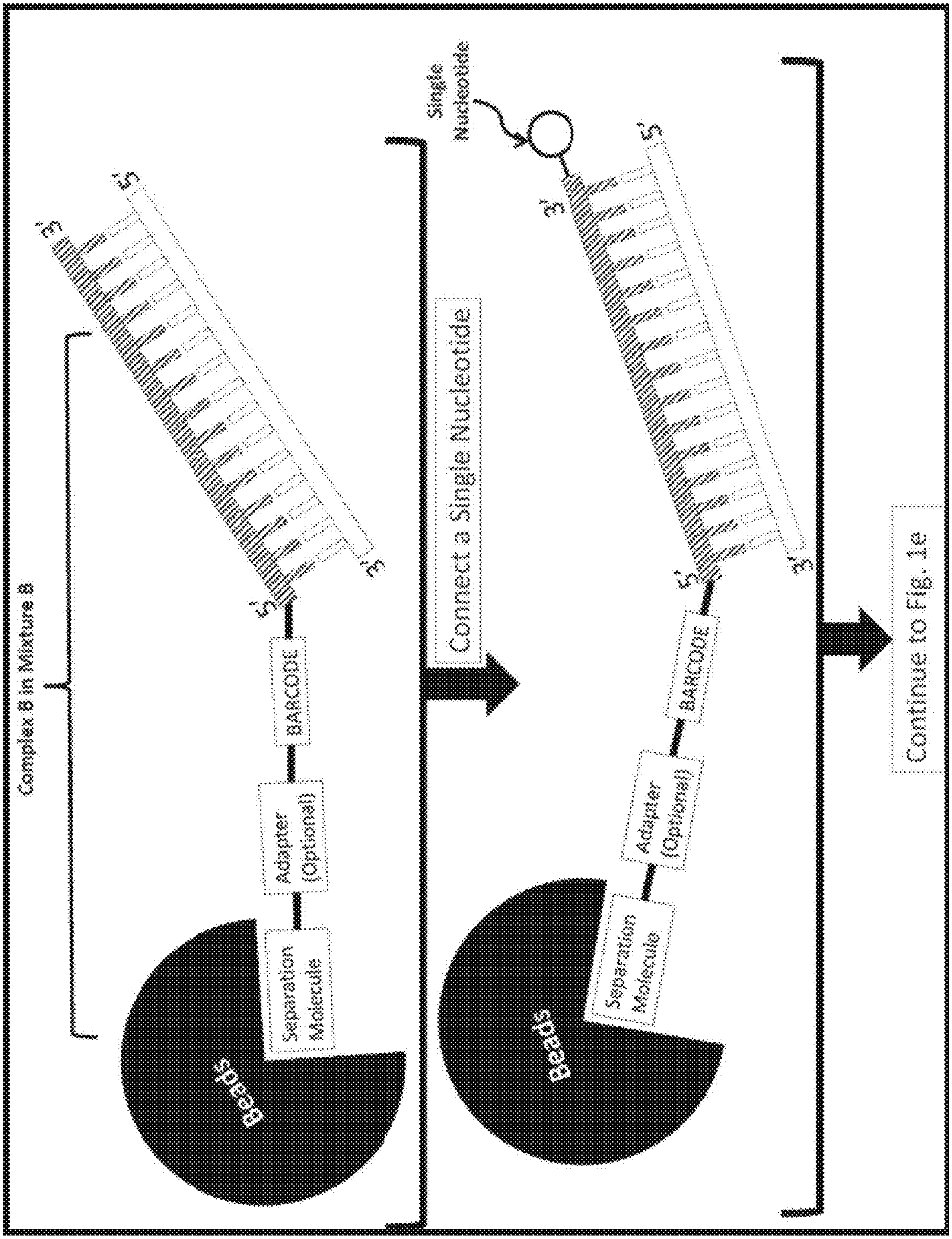

FIG. 1*d* illustrates the addition of one single nucleic acid overhang, which represents step i as follows:

i. connecting a single nucleotide to the 3' end of the single stranded elongated primer B of the double stranded complex B in the mixture B.

Figure 1E:
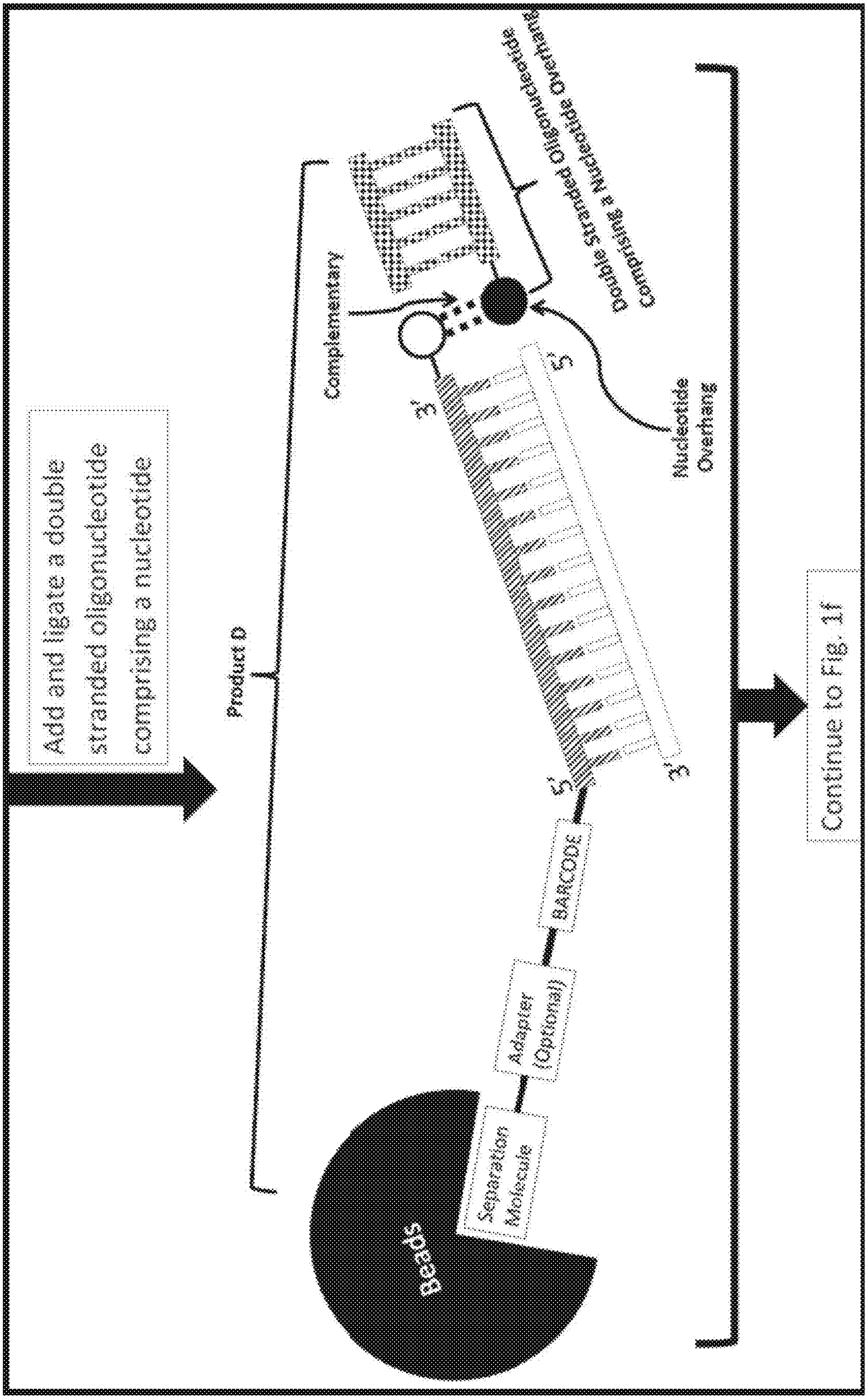

FIG. 1*e* illustrates the addition and ligation of double stranded oligonucleotide comprising a nucleic acid that is complementary to the single nucleic acid overhang in FIG. 1*d* (or step i), as follows:

j. adding a double stranded oligonucleotide to the mixture B wherein the double stranded oligonucleotide comprises a nucleotide overhang complementary to the single nucleotide of step i;

k. ligating the double stranded oligonucleotide to double stranded complex B at the 3' end of the single stranded elongated primer B and 5'end of the single stranded DNA fragment B thereby obtaining a double stranded product D.

Figure 1F:
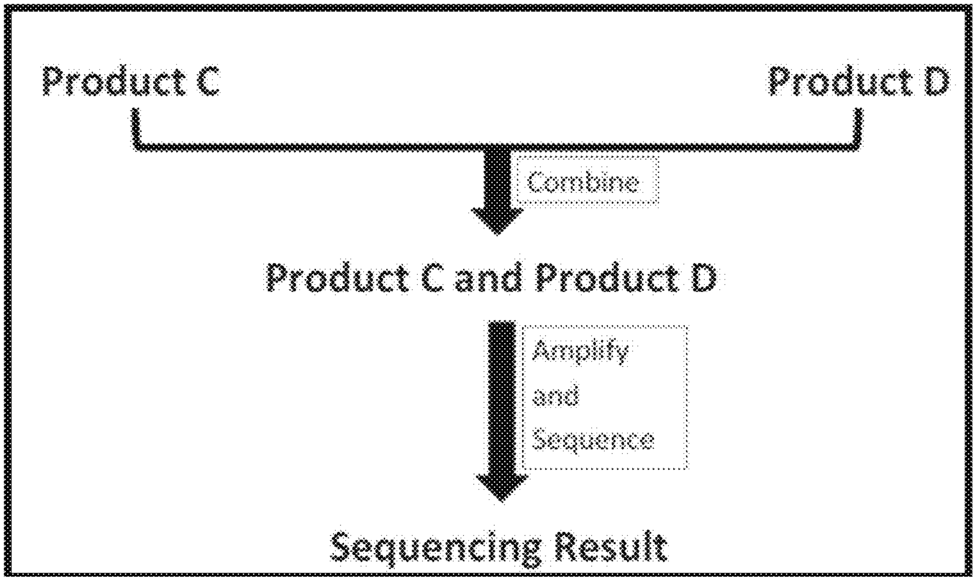

FIG. 1*f* illustrates the sequencing and data processing process of the method as described herein, which refers to steps 1 to n as follows:

l. combining the double stranded product C and the double stranded product D;
m. amplifying the double stranded product C and the double stranded product D thereby obtaining a plurality of amplicons (DNA molecules for sequencing);
n. sequencing the plurality of amplicons thereby obtaining a plurality of sequencing results;
o. using the plurality of sequencing results for:
   - identifying single nucleotide sequence variations, or small insertions, or small deletions, or copy number alteration, or deletions of homopolymeric regions, or polymorphism, or microsatellite instability within the defined target regions, or
   - identifying the structural variations within the undefined target regions, or
   - quantifying the number of distinct targets within the DNA sample.

Figure 2A:
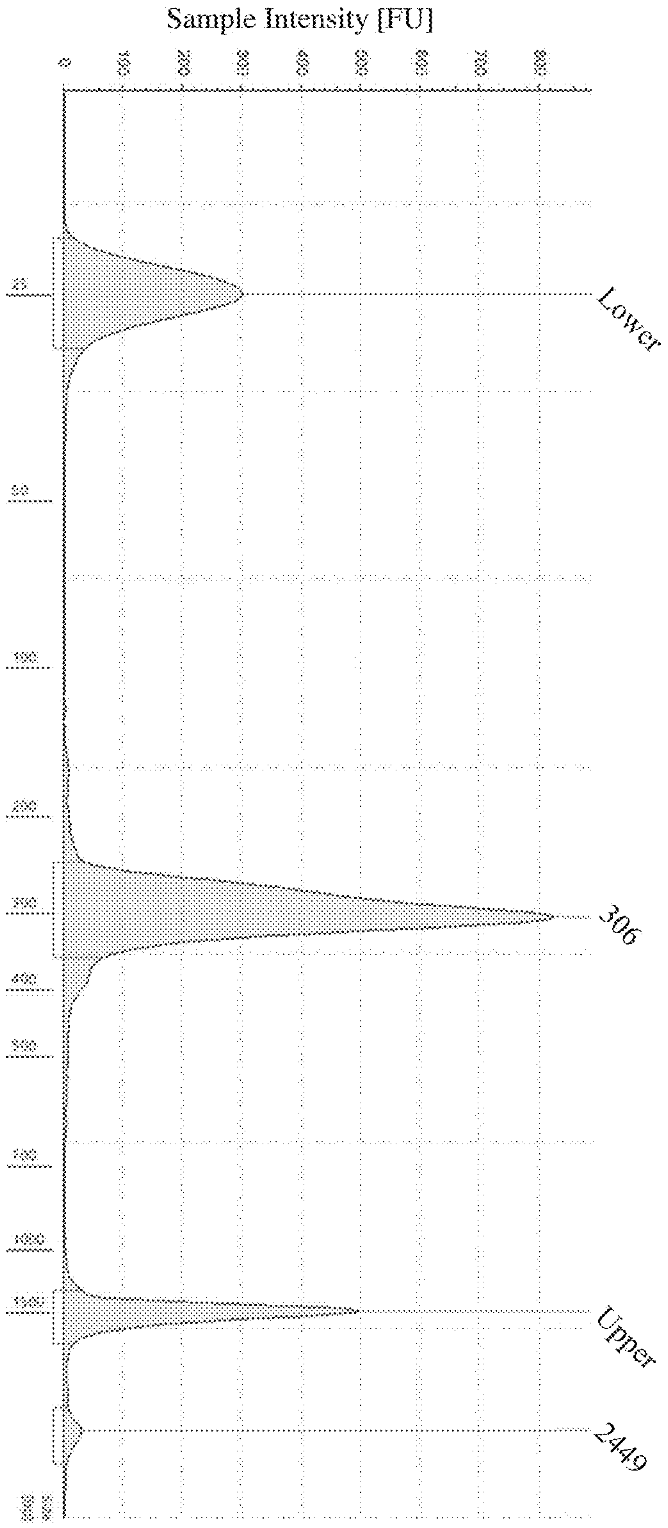
Figure 2B:
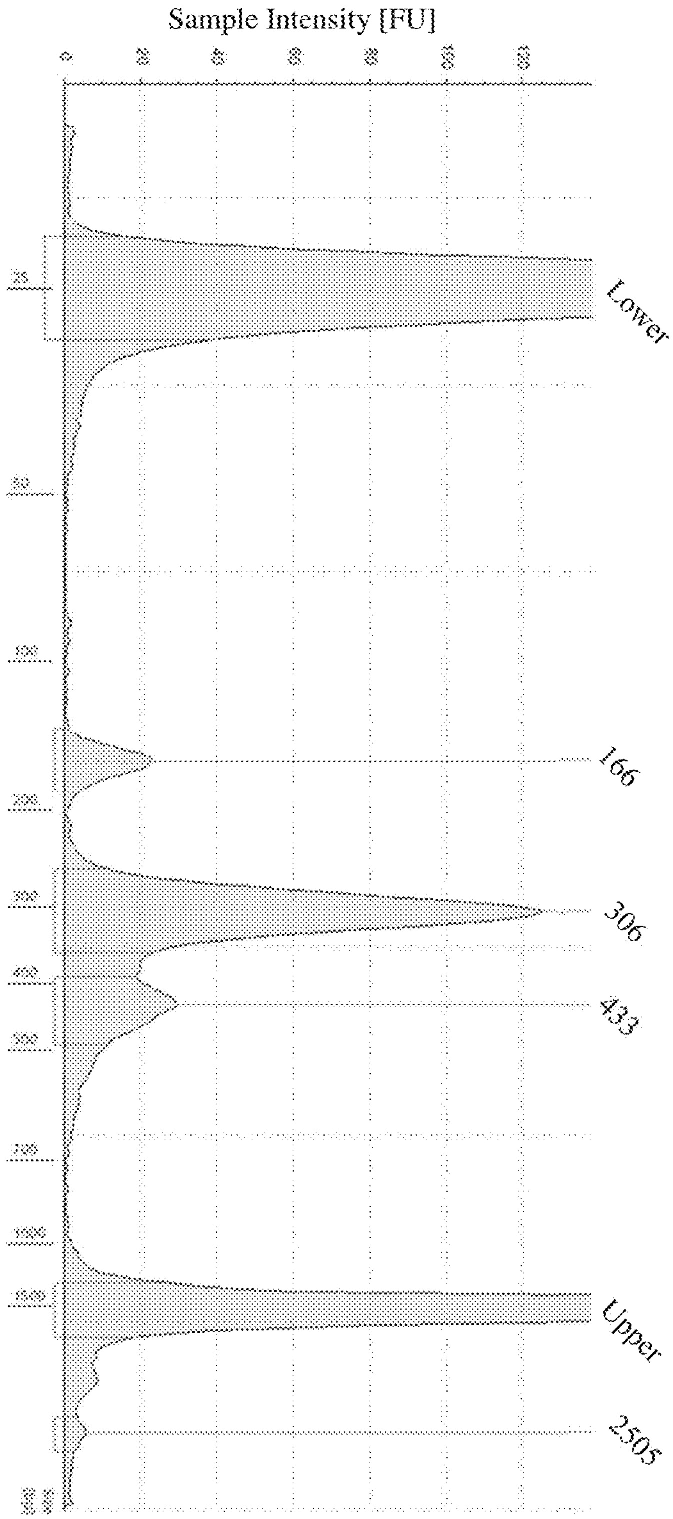

FIG. 2*a* shows illustrative examples of library generation for target amplicons generated from the same starting DNA with both ends being defined by primers. Amplicon generation is achieved by the use of a pair of primers. FIG. 2*b* shows illustrative examples of library generation for target amplicons generated from the same starting DNA with only one primer-defined end. Amplicon generation is achieved by the single-ended ligation of a double-stranded oligo adapter.

Figure 3A:
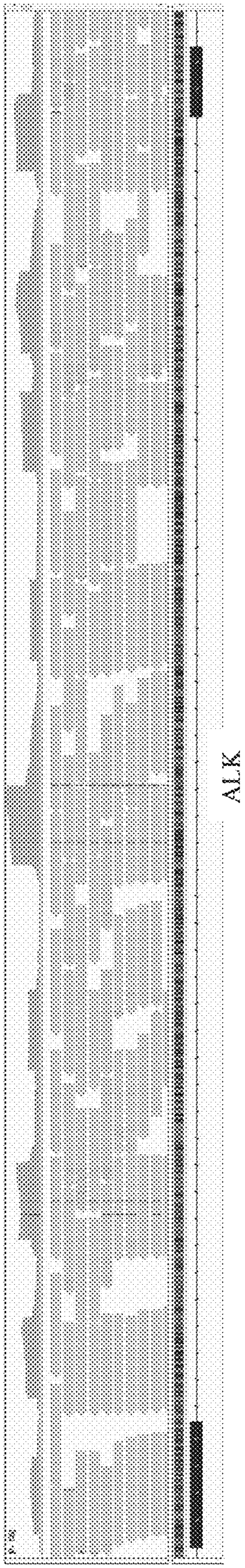
Figure 3B:
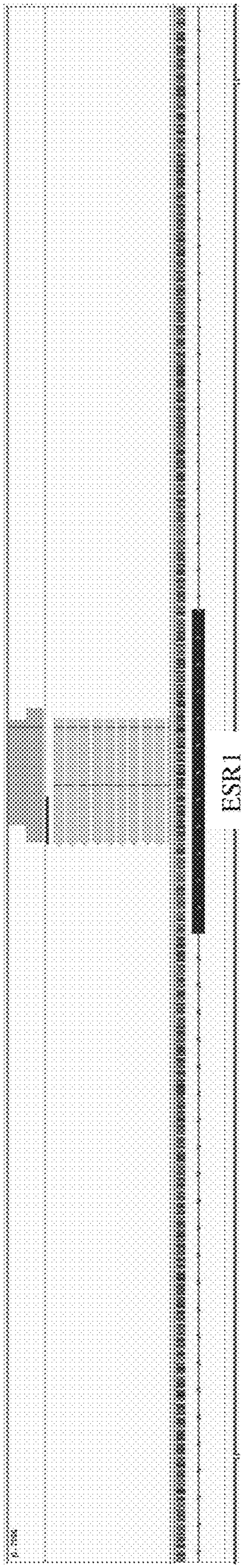

FIG. 3*a* shows an illustration of the sequencing reads mapping to the reference for amplicons generated with one primer and one ligated adapter. In FIG. 3*a* the design of target capture primers is to capture with a multiplicity of primers the region of ALK intron 19. These primers correspond to primer B in FIG. 1. FIG. 3*b* shows an illustration of the sequencing reads mapping to the reference for amplicons generated with both ends defined by primers. In FIG. 3*b* the captured region is defined by a pair of primers designed to capture a hotspot region in ESR1. The pair of primers corresponds to primer A and primer C from FIG. 1.

Figure 4B:
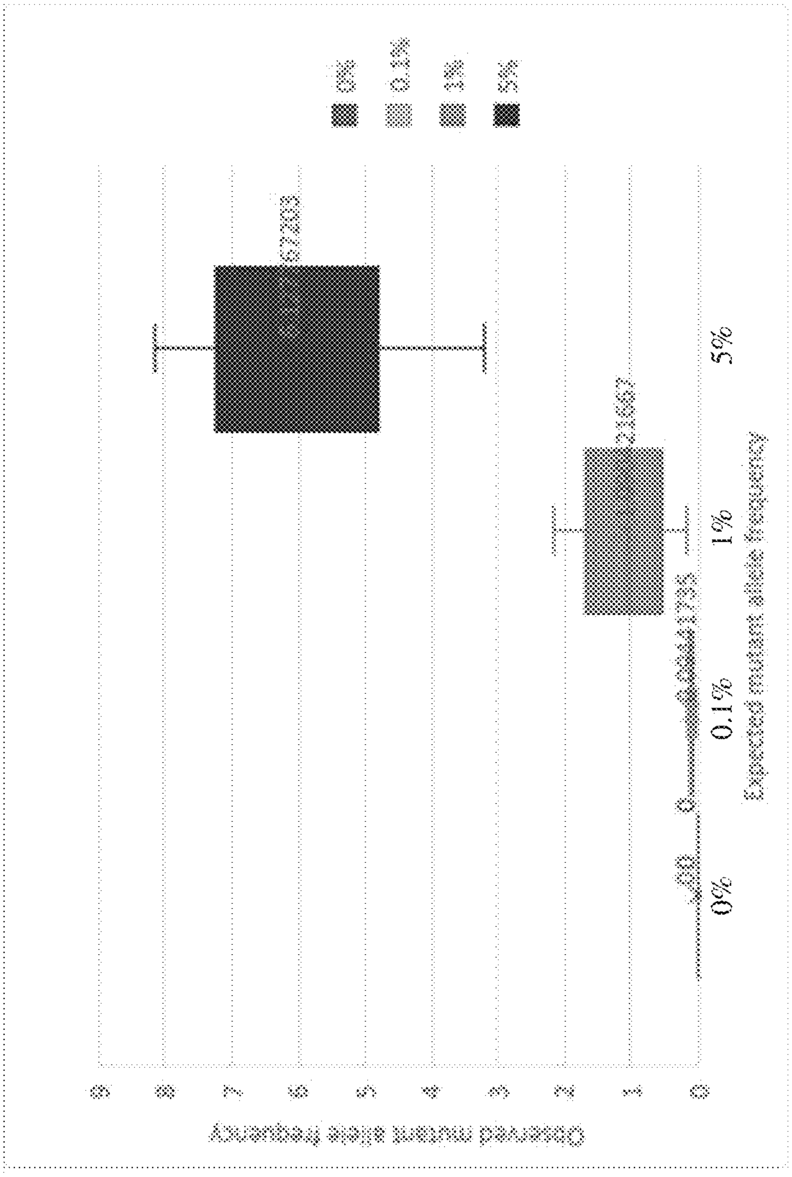

FIG. 4*a* shows a summary of Variant allele frequency (VAF) observed using the method of the present invention vs. expected frequency of variants in the Horizon Discovery™ cfDNA standards. The amount of DNA used in library preparation was 50-100 ng. FIG. 4*b* shows observed frequencies averaged across variants in the Horizon Discovery™ cfDNA standards. FIG. 4*c* shows the sensitivity of detection of true variants in the Horizon Discovery™ cfDNA standards and the specificity reported as the per-base specificity across the target panel (detection of true negatives).

Figure 5:
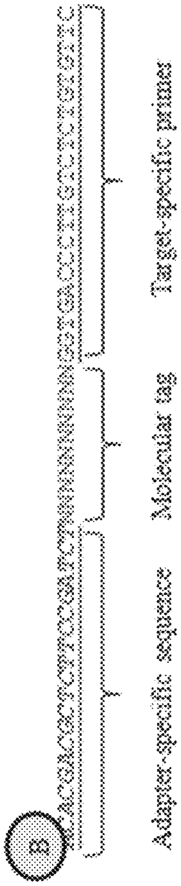

FIG. 5 shows an example of a primer B, wherein the primer B comprises a separation molecule, an adapter, a barcode, and a target-specific sequence B.

Figure 6:
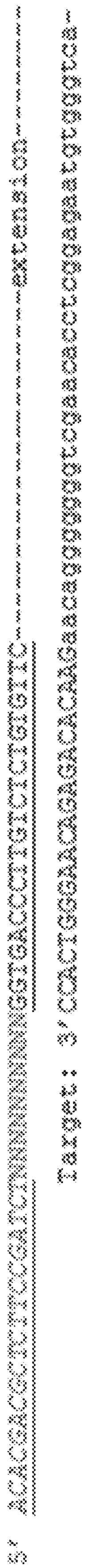

FIG. 6 shows an example of a product A with a very short target captured region shown for illustrative purposes.

Figure 7:
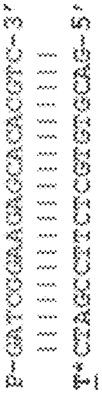

FIG. 7 shows an example of a double stranded oligonucleotide comprising a nucleotide overhang.

FIG. 8*a* shows an example of a Product D, which is obtained when a captured target goes through adapter ligation for amplicon generation as illustrated in FIG. 1*e*. FIG. 8*b* shows and an example of Product C, which is obtained when a captured target is converted to amplicon with a second primer as shown in FIG. 1*c*.

FIG. 9 shows an example of the amplification result of either Product C or Product D. Only a single strand of a double-stranded product is shown for illustrative purposes.

Figure 10A:
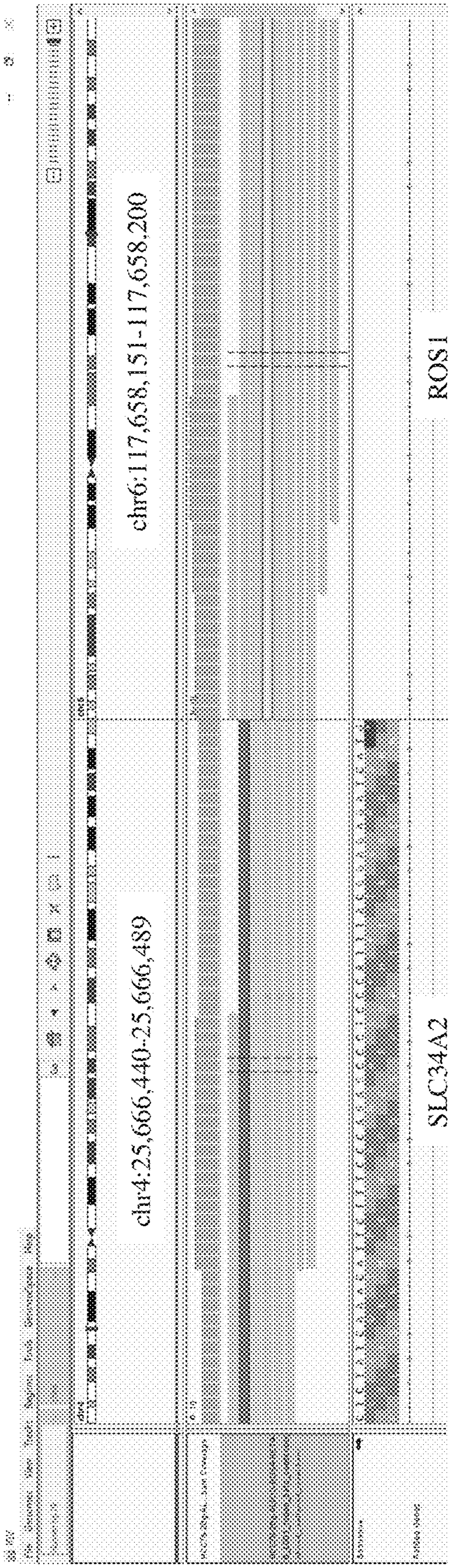
Figure 10B:
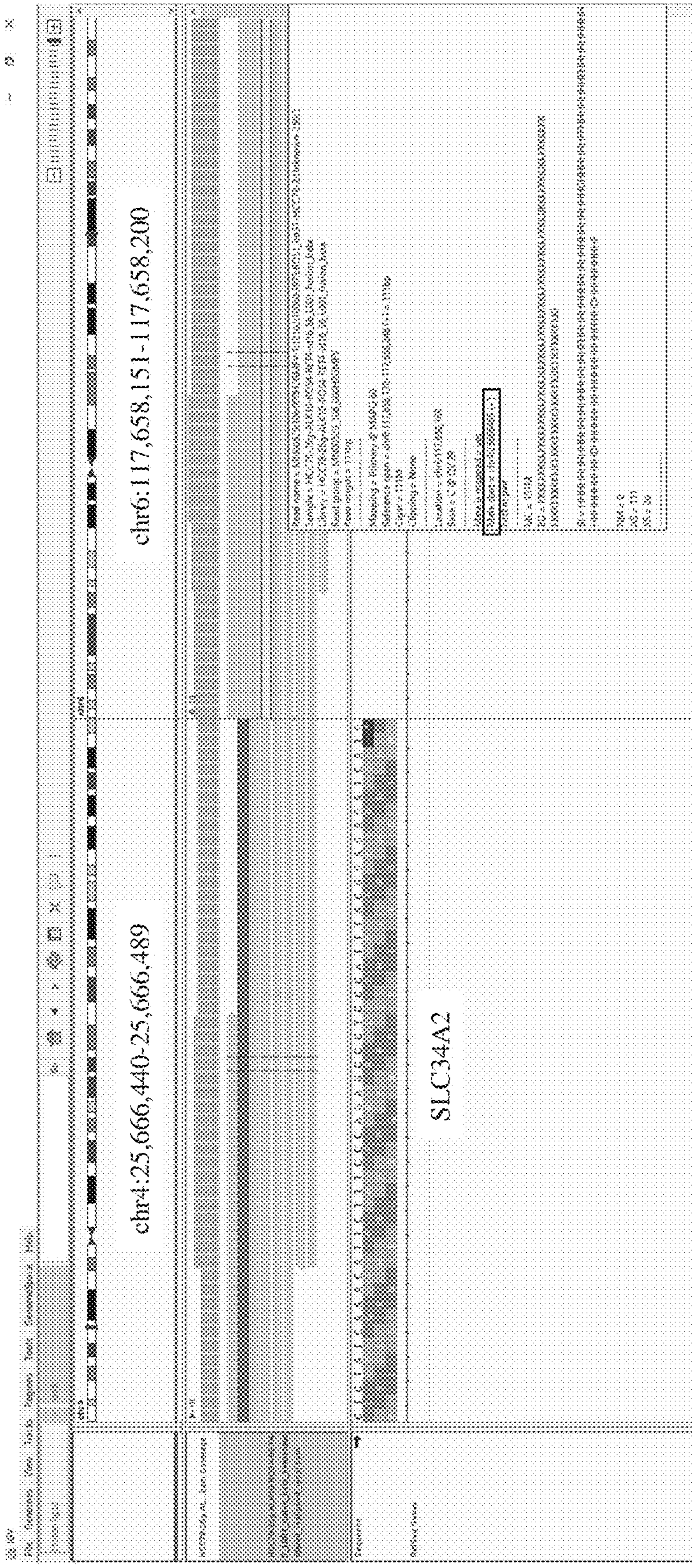

FIG. 10 is an example of using the sequencing results for the detection of fusion. FIG. 10*a* is a paired mate mapping for ROS1 gene region known to undergo fusion/rearrangement. The darker and lighter grey reads represent paired reads which have distinct mapping locations in the human genome. The right panel is the region of interest in ROS1 gene with known rearrangement. The left panel is the region that the paired read for the lighter grey read maps to and is identified as SLC34A2. FIG. 10*b* shows that the location of the paired read in SLC34A2 is chr4: 256666465, which is a distinct chromosome from the location of ALK which is chr6: 117658151. Thus, FIG. 10 shows that the method of the present invention is able to detect the fusion of SLC34A2 gene to ROS1 gene or other genes that are known to undergo rearrangements including fusions.

Figure 11A:
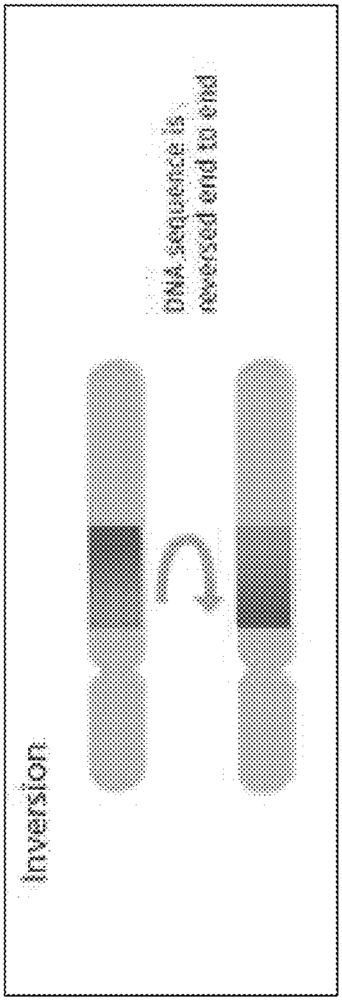
Figure 11B:
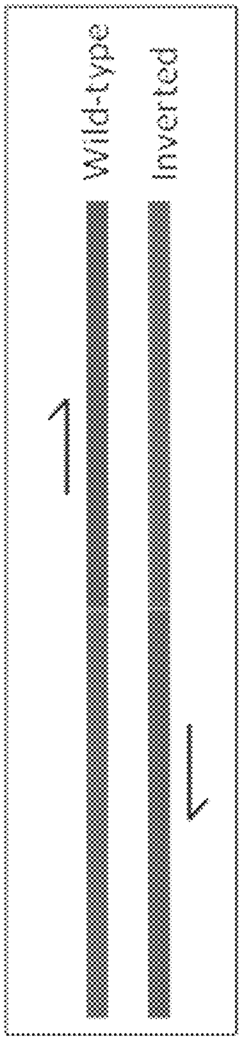

FIG. 11*a* is a schematic description of a structural variant described as an inversion, at the level of a chromosome. FIG. 11*b* is a schematic description of an inversion, compared to the wild-type condition.

Figure 12:
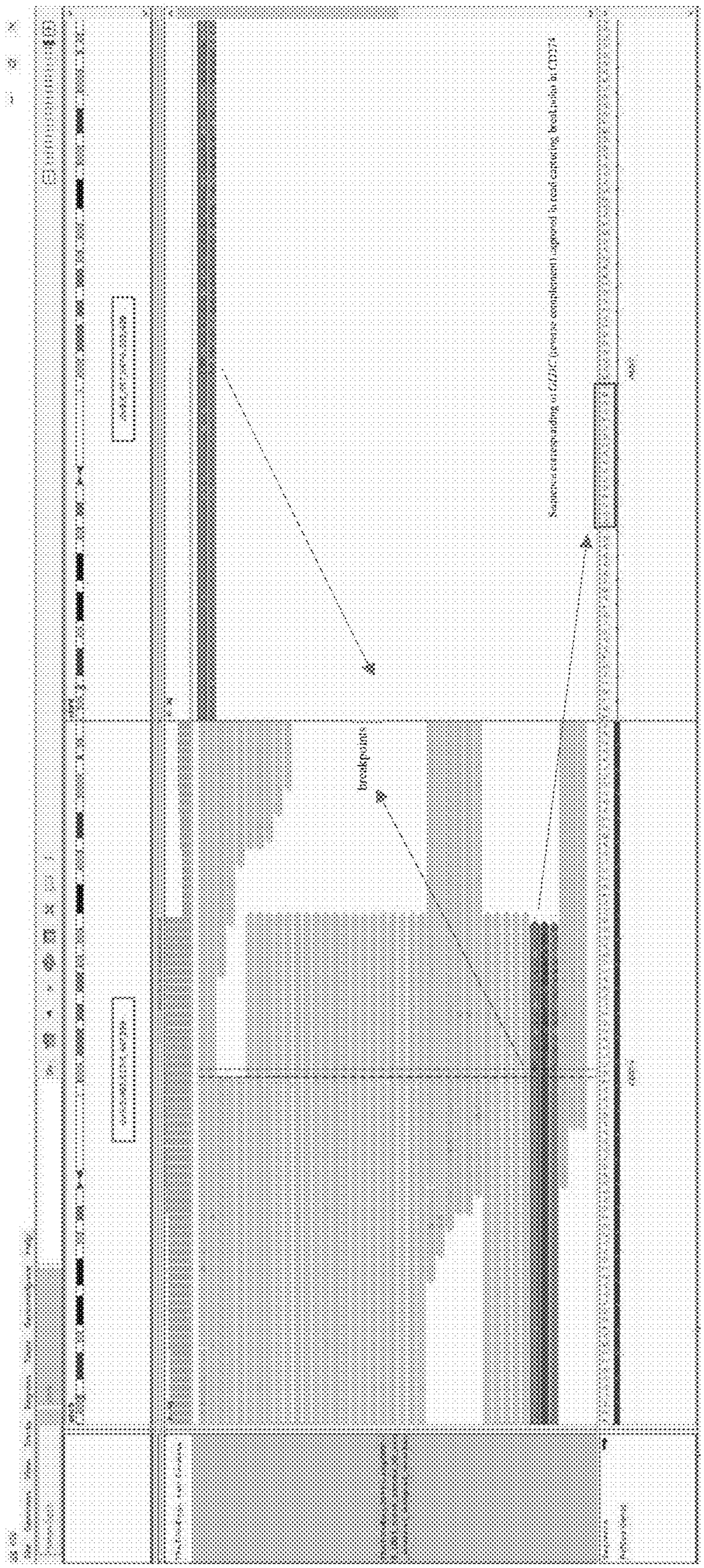

FIG. 12 shows the results of detecting an exemplary inversion in a DNA sample with known inversion variant, using the method of the invention.

Figure 13:
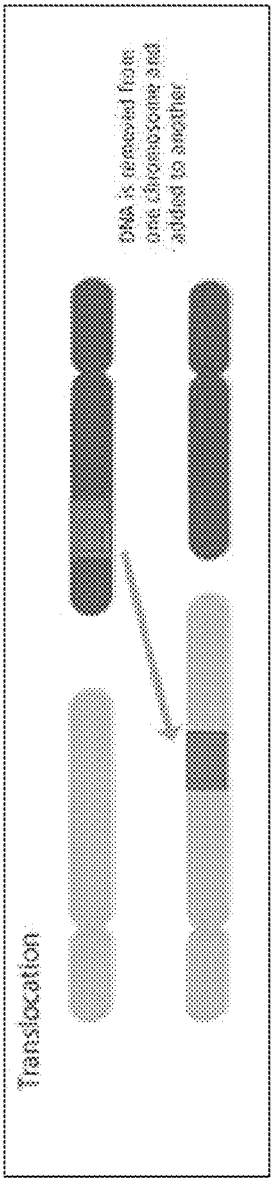

FIG. 13 is a schematic description of a structural variant described as a translocation, at the level of a chromosome.

Figure 14:
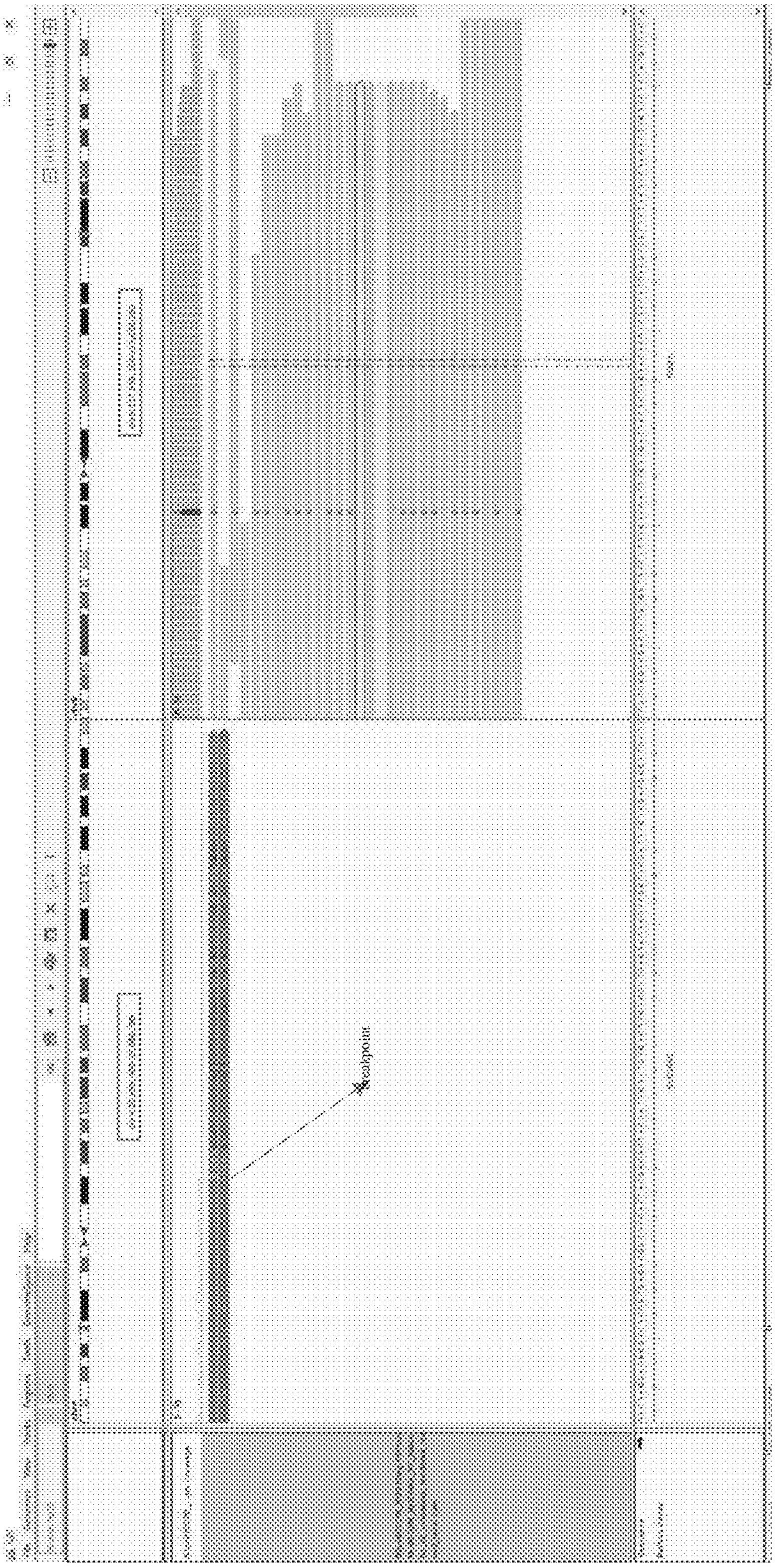

FIG. 14 shows the results of detecting an exemplary translocation in a DNA sample with known translocation variant, using the method of the invention.

FIGS. 15*a*-15*b* depict Table 2, showing mutation detection and frequency in 16 clinical samples (plasma) tested by the method of the present invention and by quantitative PCR.

FIGS. 16*a*-16*e* depict Table 3, showing detection of Epstein Barr Virus (EBV) microbial DNA targets BAMHI-W and EBNA1, in clinical samples (plasma) by the method of the present invention and qPCR.

DETAILED DESCRIPTION

The platform technology allows the simultaneous capture of targeted regions of the human and/or viral genome, as defined by pairs of primers, and of regions not defined by primers pairs, allowing the capture of genomic regions undergoing alterations at unspecified locations within a defined region of interest. In the capture step, a unique molecular tag (i.e. barcode sequence) is attached to each target DNA molecule being captured. The molecular tag (i.e. barcode sequence) allows the tracking of each target DNA fragment as it undergoes sequencing to form a DNA library. The presence of a molecular tag (i.e. barcode sequence) is detected using bioinformatics methods known in the art to count and assign each target DNA sequence from high-throughput sequencing to an original DNA molecule from the sample, carrying the same molecular tag (i.e. barcode sequence). The molecular tags (i.e. barcode sequence) are used to define molecular families, each member of which should carry the exact same sequence unaltered by the processes of capture and conversion to DNA library. Molecular families are then considered together for each region of interest to identify deviations from the expected DNA sequence. Precise deviations in the original nature of DNA sequence are detectable from the application of the 'agreement rule' within molecular families, where lack of agreement among members of each molecular family would result in the entire family being removed from consideration in molecular counts of a region of interest. In the absence of this rule, deviations within molecular families would erroneously lead to the conclusion of a sequence variant, when in fact the disagreement most likely arose from an inevitable process error.

Similarly, tags (i.e. barcode sequence) defining molecular families are also used to determine the number of unique molecules corresponding to each region of interest. Therefore, detection and accurate quantification of rare variants becomes possible through the precise and confident detection of molecules with variant sequence and those without. As exemplified in the Experimental Section, the method as described herein is also capable of detecting non-human genomic sequences such as microbial DNA in a mixture with human DNA.

The present invention can also be broadly illustrated by the following features. Firstly, a group of primers will bind to DNA fragments comprising the defined (or fully defined) target regions and another group of primers will bind to DNA fragments comprising the undefined (or partly defined) target regions. Secondly, the primers that annealed to the DNA fragments comprising part of the defined target region (i.e. product A) are separated from the primers that annealed to the DNA fragments comprising part of the undefined target region (i.e. product B). Thirdly, upon separation, the two products will undergo two different treatments. For product A, a reverse primer will be added. For product B, a double stranded oligonucleotide is added and ligated to the end that is not connected to the separation molecule that binds the separation beads in an earlier separation step. Fourthly, product A and product B that has been processed are recombined, amplified together, and the resulting amplicons are sequenced.

The method of the present invention is advantageous because it allows for simultaneous capture and identification of both the defined (or fully defined) target regions and the undefined (or partly defined) target regions (i.e. target regions that are prone to undergo sequence changes which are not previously characterized). The simultaneous capture allows for lesser DNA samples to be used. The reason for having a separate method for the undefined (or partly defined) target regions is that these regions cannot be captured by a pair of primers because the sequence changes can happen at positions within the target that cannot be known when the target capture is being performed (i.e. the precise location and sequence change is unknown). Because the location and the sequence change is unknown, it is not possible to use a pair of primers flanking the target region, as happens in conventional methods. Further, the use of primers and polymerase-mediated extension affords for greater specificity of target capture, compared to conventional methods based on probe hybridization.

Further to the above, another advantage that the present invention has is that despite separate workflows for converting the defined (or the fully defined) targets and the undefined (or the partly defined) targets into sequencing libraries, the method does not require initial splitting of the sample. By not requiring such splitting, the copy number of the DNA fragments that can be accessed by both the primer that targets the defined target region (i.e. primer A) and the primer that targets the undefined target region (i.e. primer B) is not reduced.

Thus, in one aspect, the present invention provides a method of simultaneously capturing and identifying distinct targets within a DNA sample, wherein the distinct targets comprise a defined (or a fully defined) target region and an undefined (or a partly defined) target region, wherein the undefined (or the partly defined) target region comprises structural variations or rearrangement or fusion, comprising the steps of:

a. providing a main mixture comprising a plurality of double stranded DNA fragments A, a plurality of double stranded DNA fragments B, a polymerase, a primer A, and a primer B, wherein:
   - the double stranded DNA fragment A is a double stranded DNA fragment comprising a part of the defined (or the fully defined) target region;
   - the double stranded DNA fragment B is a double stranded DNA fragment comprising a part of the undefined (or the partly defined) target region;
   - the primer A comprises, a barcode sequence, and a target-specific sequence A,
     - wherein the target-specific sequence A is an oligonucleotide complementary to a sequence at/close to the 3' end of a single strand of the double stranded DNA fragment A;

and
   - the primer B comprises a separation molecule, a barcode sequence, and a target-specific sequence B,
     - wherein the target-specific sequence B is an oligonucleotide complementary to a sequence within a single strand of the double stranded DNA fragment B, b. denaturing the double stranded DNA fragment A and the double stranded DNA fragment B thereby allowing the primer A to anneal to a single stranded DNA fragment A and the primer B to anneal to the a single stranded DNA fragment B;

c. allowing the polymerase to elongate the primer A and the primer B thereby obtaining a double stranded product A and a double stranded product B, wherein:
   - the double stranded product A is a single stranded elongated primer A that is annealed to the single stranded DNA fragment A and
   - the double stranded product B is a single stranded elongated primer B that is annealed to the single stranded DNA fragment B;

d. adding a bead that binds the separation molecule to the main mixture and allowing the separation molecule in the double stranded product B to bind to the bead thereby forming a double stranded complex B;

e. separating the double stranded product A and the double stranded complex B in the main mixture thereby obtaining a mixture A and a mixture B, wherein:
   - the mixture A comprises the double stranded product A and
   - the mixture B comprises the double stranded complex B;

f. adding a primer C to the mixture A, wherein the primer C comprises a target-specific sequence C,
   - wherein the target-specific sequence C is an oligonucleotide complementary to a sequence at/close to the 3' end of the single stranded elongated primer A;

g. denaturing the double stranded product A in the mixture A thereby allowing the primer C to anneal to the single stranded elongated primer A;

h. allowing the polymerase to elongate the primer C thereby obtaining a double stranded product C, wherein the double stranded product C is a single stranded elongated primer C that is annealed to the single stranded elongated primer A;

i. connecting a single nucleotide to the 3' end of the single stranded elongated primer B of the double stranded complex B in the mixture B;

j. adding a double stranded oligonucleotide to the mixture B wherein the double stranded oligonucleotide comprises a nucleotide overhang complementary to the single nucleotide of step i;

k. ligating the double stranded oligonucleotide to double stranded complex B at the 3' end of the single stranded elongated primer B and 5'end of the single stranded DNA fragment B thereby obtaining a double stranded product D;

l. combining the double stranded product C and the double stranded product D;

m. amplifying the double stranded product C and the double stranded product D thereby obtaining a plurality of amplicons (or DNA molecules for sequencing);

n. sequencing the plurality of amplicons thereby obtaining a plurality of sequencing result;

o. using the plurality of sequencing results for:
 - identifying single nucleotide sequence variations, or small insertions, or small deletions, or copy number alteration, or deletions of homopolymeric regions, or polymorphism, or microsatellite instability within the defined (or the fully defined) target regions, or
 - identifying the structural variations within the undefined (or the partly defined) target regions, or
 - quantifying the number of distinct targets within the DNA sample.

In one example, the present invention provides a method of simultaneously identifying a defined region and an undefined region within a DNA sample, wherein the undefined region comprises a structural variation, comprising the steps of:

a. providing a main mixture comprising a plurality of double stranded DNA fragments A, a plurality of double stranded DNA fragments B, a polymerase, a primer A, and a primer B, wherein:
 - the double stranded DNA fragment A is a double stranded DNA fragment comprising a part of the defined region;
 - the double stranded DNA fragment B is a double stranded DNA fragment comprising a part of the undefined region;
 - the primer A comprises, a barcode sequence, and a target-specific sequence A,
   - wherein the target-specific sequence A is an oligonucleotide complementary to a sequence at/close to the 3' end of a single strand of the double stranded DNA fragment A; and
 - the primer B comprises a separation molecule, a barcode sequence, and a target-specific sequence B,
   - wherein the target-specific sequence B is an oligonucleotide complementary to a sequence within a single strand of the double stranded DNA fragment B, b. denaturing the double stranded DNA fragment A and the double stranded DNA fragment B thereby allowing the primer A to anneal to a single stranded DNA fragment A and the primer B to anneal to the a single stranded DNA fragment B;

c. allowing the polymerase to elongate the primer A and the primer B thereby obtaining a double stranded product A and a double stranded product B, wherein:
 - the double stranded product A is a single stranded elongated primer A that is annealed to the single stranded DNA fragment A and
 - the double stranded product B is a single stranded elongated primer B that is annealed to the single stranded DNA fragment B;

d. adding a bead that binds the separation molecule to the main mixture and allowing the separation molecule in the double stranded product B to bind to the bead thereby forming a double stranded complex B;

e. separating the double stranded product A and the double stranded complex B in the main mixture thereby obtaining a mixture A and a mixture B, wherein:
 - the mixture A comprises the double stranded product A and
 - the mixture B comprises the double stranded complex B;

f. adding a primer C to the mixture A, wherein the primer C comprises a target-specific sequence C,
 - wherein the target-specific sequence C is an oligonucleotide complementary to a sequence at/close to the 3' end of the single stranded elongated primer A;

g. denaturing the double stranded product A in the mixture A thereby allowing the primer C to anneal to the single stranded elongated primer A;

h. allowing the polymerase to elongate the primer C thereby obtaining a double stranded product C, wherein the double stranded product C is a single stranded elongated primer C that is annealed to the single stranded elongated primer A;

i. connecting a single nucleotide to the 3' end of the single stranded elongated primer B of the double stranded complex B in the mixture B;

j. adding a double stranded oligonucleotide to the mixture B wherein the double stranded oligonucleotide comprises a nucleotide overhang complementary to the single nucleotide of step i;

k. ligating the double stranded oligonucleotide to double stranded complex B at the 3' end of the single stranded elongated primer B and 5' end of the single stranded DNA fragment B thereby obtaining a double stranded product D;

l. combining the double stranded product C and the double stranded product D;

m. amplifying the double stranded product C and the double stranded product D thereby obtaining a plurality of amplicons (or DNA molecules for sequencing);

n. sequencing the plurality of amplicons thereby obtaining a plurality of sequencing results;

o. using the plurality of sequencing results for:
 - identifying single nucleotide sequence variations, or small insertions, or small deletions, or copy number alteration, or deletions of homopolymeric regions, or polymorphism, or microsatellite instability within the defined target regions, or
 - identifying the structural variations within the undefined target regions, or
 - quantifying the number of distinct targets within the DNA sample.

For example, the method as described herein is illustrated by the schematic diagrams presented in FIG. 1. That is, FIG. 1*a* describes steps a and b of the method as described herein, which are:

a. providing a main mixture comprising a plurality of DNA fragments A, a plurality of DNA fragments B, a polymerase, a primer A, and a primer B, wherein:
 - the DNA fragment A is a DNA fragment comprising a part of the defined region;
 - the DNA fragment B is a DNA fragment comprising a part of the undefined region;
 - the primer A comprises, a barcode sequence, and a target-specific sequence A, wherein the target-specific sequence A is an oligonucleotide complementary to a sequence at/close to the 3' end of a DNA fragment A; and the primer B comprises a separation molecule, a barcode sequence, and a target-specific sequence B, wherein the target-specific sequence B is an oligonucleotide complementary to a sequence within a DNA fragment B, b. denaturing the DNA fragment A and the DNA fragment B thereby allowing the primer A to anneal to a DNA fragment A and the primer B to anneal to the DNA fragment B.

FIG. 1*b* describes steps c to e as follows:

c. allowing the polymerase to elongate the primer A and the primer B thereby obtaining a double stranded product A and a double stranded product B, wherein:

the double stranded product A is a single stranded elongated primer A that is annealed to the DNA fragment A and the double stranded product B is a single stranded elongated primer B that is annealed to the DNA fragment B;

d. adding a bead that binds the separation molecule to the main mixture and allowing the separation molecule in the double stranded product B to bind to the bead thereby forming a double stranded complex B;

e. separating the double stranded product A and the double stranded complex B in the main mixture thereby obtaining a mixture A and a mixture B, wherein:

the mixture A comprises the double stranded product A and the mixture B comprises the double stranded complex B.

FIG. 1*c* illustrates steps f to h as follows:

f. adding a primer C to the mixture A, wherein the primer C comprises a target-specific sequence C, wherein the target-specific sequence C is an oligonucleotide complementary to a sequence at/close to the 3' end of the single stranded elongated primer A;

g. denaturing the double stranded product A in the mixture A thereby allowing the primer C to anneal to the single stranded elongated primer A;

h. allowing the polymerase to elongate the primer C thereby obtaining a double stranded product C, wherein the double stranded product C is a single stranded elongated primer C that is annealed to the single stranded elongated primer A.

FIG. 1*d* illustrates the addition of one single nucleic acid overhang, which represents step I as follows:

i. connecting a single nucleotide to the 3' end of the single stranded elongated primer B of the double stranded complex B in the mixture B.

FIG. 1*e* illustrates the addition and ligation of double stranded oligonucleotide comprising a nucleic acid that is complementary to the single nucleic acid overhang in FIG. 1*d* (or step i), as follows:

j. adding a double stranded oligonucleotide to the mixture B wherein the double stranded oligonucleotide comprises a nucleotide overhang complementary to the single nucleotide of step i;

k. ligating the double stranded oligonucleotide to double stranded complex B at the 3' end of the single stranded elongated primer B and 5' end of the single stranded DNA fragment B thereby obtaining a double stranded product D.

FIG. 1*f* illustrates the sequencing and data processing process of the method as described herein, which refers to steps 1 to n as follows:

l. combining the double stranded product C and the double stranded product D;

m. amplifying the double stranded product C and the double stranded product D thereby obtaining a plurality of amplicons (or DNA molecules for sequencing);

n. sequencing the plurality of amplicons thereby obtaining a plurality of sequencing result;

o. using the plurality of sequencing results for:

identifying single nucleotide sequence variations, or small insertions, or small deletions, or copy number alteration, or deletions of homopolymeric regions, or polymorphism, or microsatellite instability within the defined target regions, or identifying the structural variations within the undefined target regions, or quantifying the number of distinct targets within the DNA sample.

As used herein, the term "defined region" is defined as a region in a DNA fragment that is free of structural variations that may be found in the undefined region (i.e. structural variations that are not previously characterized). That is, the "defined region" comprises a region of DNA fragment that structurally is identical to or substantially the same as DNA fragments from a reference sequence. In other words, a "fully defined target region" is a target for which the sequence identity (i.e. the start and end of the target) are fully defined prior to capture. In the present disclosure, the term "defined region", "defined target region", and "fully defined target region" are used interchangeably. Thus, it would be understood by the person skilled in the art that the term "undefined region" would encompass a region of DNA fragment that has structural variations that are not previously characterized. In other words, "partly defined target region" is a target for which the sequence identity is not fully defined prior to target capture and comprises target region prone to undergo sequence changes (such as structural rearrangements). It is appreciated that the precise sequence composition of a "partly defined target region" cannot be predetermined and thus it may be impossible to design a pair of defining primers for such region. The sequence definition of an "undefined region", or a "partly defined target region", such as detection of genomic rearrangements with unknown fusion partners, is determinable only once the sequencing results are obtained. It would also be apparent to the person skilled in the art that the defined region and undefined region would have different DNA sequences. Thus, in some examples, the target specific sequence A and the target specific sequence B do not overlap. As would be understood by the person skilled in the art, the term "undefined target region" does not mean that 100% of the DNA sequence within the target region is unknown in the art. As used herein, the "undefined target region" refers to a target region wherein about 5%, or about 10%, or about 20%, or about 30%, or about 40%, or about 50%, or about 60%, or about 70%, or about 80%, or about 90%, or about 95% of the DNA sequence within the target region is unknown in the art. In the present disclosure, the term "undefined region", "undefined target region", and "partly defined target region" are used interchangeably. As used herein, the term "barcode sequence" is a commonly used term in the art of nucleic acid sequencing and used within the definition as known in the art. Thus, the term "barcode sequence" refers to the encoded molecules or barcodes that include variable amount of information within the nucleic acid sequence. For example, the barcode sequence is a tag that can be read out using any of a variety of sequence identification techniques, for example, nucleic acid sequencing, probe hybridization based assay, and the like. In some examples, the barcode sequence is used in the method as described herein to append different target specific sequences, such that when the barcode sequence and target specific sequence anneal to the (target) DNA fragment, each different (target) DNA fragment would then have a unique barcode sequence that is attached to it and read out with the sequence of the (target) DNA fragment from that sample. The barcode sequence allows the pooled analysis of multiple unique DNA fragments, where the resulting sequence information from the pool can be later attributed back to each starting DNA fragment. That is, after the process of amplification, the barcode sequence is used to group amplicons to form a family of amplicons having the same oligonucleotide with a randomly assigned nucleic acid sequence (i.e. same barcode oligonucleotide). In some examples, the barcode sequence is an overhang that does not complement any sequence within DNA fragment A and DNA fragment B. In some examples, the barcode sequence may be an oligonucleotide comprising 10 to 16 random nucleotides, or 10 to 15 random nucleotides, or 10 to 13 random nucleotides, or 8 random nucleotides, or 11 random nucleotides, or 12 random nucleotides, or 13 random nucleotides, or 14 random nucleotides, or 15 random nucleotides, or 16 random nucleotides. In one example, the barcode sequence is an oligonucleotide comprising 10 random nucleotides. As exemplified in the Experimental Section, the barcode sequence may be defined as NNNNNNNNNN (SEQ ID NO: 1), which may have the sequences such as, but is not limited to, CATTACATAC (SEQ ID NO: 2), GCGTGGACAA (SEQ ID NO: 3), TTTTTAGACA (SEQ ID NO: 4), TAAGAGGTCC (SEQ ID NO: 5), and the like.

As used herein, the term "at the 3' end" corresponds to the last nucleotide of a single DNA strand. As used herein, the term "close to the 3' end" corresponds to a distance of from 1 to 100 nucleotides, or from 5 to 90 nucleotides, or from 10 to 80 nucleotides, or from 15 to 70 nucleotides, or from 20 to 60 nucleotides, or about 1 nucleotides, or about 5 nucleotides, or about 10 nucleotides, or about 15 nucleotides, or about 20 nucleotides, or about 25 nucleotides, or about 30 nucleotides, or about 35 nucleotides, or about 40 nucleotides, or about 50 nucleotides, or about 60 nucleotides, or about 70 nucleotides, or about 80 nucleotides, or about 90 nucleotides, or about 100 nucleotides from the 3' end of a single DNA strand. In one example, when the term "close to the 3' end" is used to define a reverse primer, the binding site of the reverse primer (for example, primer C) is predetermined such that the overall length of the target region defined by combination of the forward primer (for example primer A) and the reverse primer is from 80 base pairs (bp) to 200 bp, or from 100 bp to 180 bp, or from 120 bp to 160 bp, or from 140 bp to 150 bp, or about 80 bp, or about 90 bp, or about 100 bp, or about 110 bp, or about 120 bp, or about 130 bp, or about 140 bp, or about 150 bp, or about 160 bp, or about 170 bp, or about 190 bp, or about 200 bp.

In regard to step i of the present invention (i.e. the step of connecting a single nucleotide to the 3' end of the single stranded elongated primer B of the double stranded complex B in the mixture B), a person skilled in the art is aware that the single nucleotide that is to be connected with the 3' end of the single stranded elongated primer B can be any nucleotide. In one example, the single nucleotide may include, but is not limited to, adenine (A), cytosine (C), guanine (G), thymine (T), and the like. In one example, wherein when the single nucleotide to be connected is adenine (A), Taq polymerase is used and the connecting step is known as "A-tailing". The A-tailing step exploits the intrinsic terminal transferase activity of Taq polymerase by which it catalyzes the template-independent addition of an adenine residue to the 3' end of both strands of DNA molecules. In the presence of a mixture of four dNTPs, dA is added preferentially to 3' end of DNA molecule by Taq polymerase. Other nucleotides can be added but would require differing reaction conditions for Taq activity. Therefore, under standard reaction conditions, in the presence of dNTPs, Taq polymerase will preferentially incorporate dA to the 3' end of the DNA molecules.

As the method as described herein utilises sequencing platforms/methods known in the art, it would be apparent to the person skilled in the art that the DNA fragment processed through the steps of the method as described herein may have to be prepared to comprise additional nucleic acid sequences recognised by the sequencing platforms/methods (i.e. adapter sequences). Thus, in some examples, the primer A, the primer B, the primer C and/or the double stranded oligonucleotide further comprises an adapter sequence.

As used herein, the term "adapter sequence" refers to an oligonucleotide sequence bound to the 5' and 3' end of each DNA fragment in a sequencing library. The adapter sequences are complementary to the plurality of oligonucleotide present on the surface of flow cells of the sequencing tools thereby allowing the DNA fragment to attach to the sequencing tools. In some examples, when the sequencing utilized is Illumina Sequencing (i.e. Illumina® sequencing technology), the adapter may be a universal P5 adapter as follows: AATGATACGGCGACCACCGAGATCT (SEQ ID NO: 13), and/or an indexed P7 adapter as follows: CAAGCAGAAGACGGCATACGAGAT (SEQ ID NO: 14) (see Table 1).

As described herein, the distinct targets within the DNA sample that can be simultaneously captured and identified by the method of the present comprises a defined target region (or a fully defined target region) and an undefined target region (or a partly defined target region). In one example, the undefined target region (or the partly defined target region) comprises structural variations or rearrangement or fusion, which are not previously characterized. In one example, the undefined target region (or the partly defined target region) is prone to undergo a structural rearrangement or sequence changes. As used herein, the term "structural variations" refers to variations in the structure of the genome—i.e. in the order of sections of the DNA (as opposed to the smaller variation to the sequence alone which maintains the overall order to the DNA sections with respect to the genome). As used herein, the term "rearrangement" refers to—rearrangements in the order of sections of the DNA (interchangeable with "structural variations"). As used herein, the term "fusion" refers to structural variants produced through interchromosomal or intrachromosomal rearrangements. In one example, the structural variations may include, but are not limited to, deletion, duplication, insertion, inversion, transversion, translocation, and the like. As used herein, the term "deletion" refers to a sequence change where more than 50 nucleotides are removed. As used herein, the term "duplication" refers to a sequence change where a copy of one or more nucleotides are inserted directly 3'-flanking of the original copy. As used herein, the term "insertion" refers to a sequence change where more than 50 nucleotides are inserted between two nucleotides but where the insertion is not a copy of a sequence immediately 5'-flanking. As used herein, the term "inversion" refers to a sequence change where more than one nucleotide replacing the original sequence are the reverse complement of the original sequence. As used herein, the term "translocation" refers to rearrangement of parts between non-homologous chromosomes, which can result in "fusion".

As would be apparent to the person skilled in the art, the method as described herein can also be used to detect single nucleotide variations such as substitution. In some examples, the sequencing result is further used to detect a single nucleotide variation. In some examples, the sequencing result is further used to detect a single nucleotide variation within the undefined target region (or the partly defined target region). In some examples, the sequencing result is further used to detect a single nucleotide variation within the defined target region (or the fully defined target region). As used herein, the term "single nucleotide variation", "single nucleotide sequence variation", and "point mutation" may be used interchangeably.

In one example, the defined target region (or the fully defined target region) comprises single nucleotide sequence variations, small insertion, small deletion, genomic copy number alteration, deletion of homopolymeric region, foreign DNA sequences (e.g. wherein the DNA sample is human DNA, microbial DNA sequences are considered foreign DNA sequence), polymorphisms or single-nucleotide variations in microbial DNA sequence, and the like. In one example, the deletion of homopolymeric region may include but is not limited to microsatellite instability. As used herein, the term "single nucleotide sequence variations" or "single nucleotide variations" refers to variation in a single nucleotide that occurs at a specific position in the genome, differing from the nucleotide defining the position in the reference genome. As used herein, the term "small insertion" refers to a sequence change where less than 50 nucleotides are inserted between two nucleotides but where the insertion is not a copy of a sequence immediately 5'-flanking. As used herein, the term "small deletion" refers to a sequence change where less than 50 nucleotides are removed. As used herein, the term "copy number alteration" refers to the repetition of sections of the genome (duplication) or loss of sections of the genome (deletion). As used herein, the term "deletions of homopolymeric regions" refers to the shortening of a homopolymeric tracts in the genome. An example of "deletions of homopolymeric region" is GCGAAAAAAAAAAAAAAATA becomes GCGAAATA, this a deletion of 12 A's from the homopolymeric tract of 15 A's. As used herein, the term "polymorphism" refers to a variation in a single nucleotide that occurs at a specific position in the genome, and is a variation in all copies of the organism's genome, differing from nucleotide defining the position in the organism's population (reference). As used herein, the term "microsatellite instability" refers to genetic instability in short nucleotide repeats or microsatellite, which is a tract of tandemly repeated (i.e. adjacent) DNA motif ranging from one to six or up to ten nucleotides, with each motif repeated 5 to 50 repeated times. A person skilled in the art is aware that the sum of all of the variants within the defined target region (or the fully defined target region) is known as total mutation (or variant) load or tumour mutational burden (TMB). A person skilled in the art is also aware that determining the total mutation (or variant) load or tumour mutational burden (TMB) is useful in determining the therapeutic target of certain diseases (such as cancer).

The method of the present disclosure can also be used to detect certain diseases. Thus, in one example, the DNA sample for the method of the present disclosure is obtained from a subject having and/or suspected of having a disease. In some examples, the disease may include, but is not limited to cancer, infectious disease, and the like. In some examples, the cancer may include, but is not limited to, lung cancer, colorectal cancer, breast cancer, pancreatic cancer, prostate cancer, nasopharyngeal cancer, liver cancer, cholangiocarcinoma, esophageal cancer, urothelial cancer, gastrointestinal cancer, and the like. In some examples, the infectious diseases may include, but is not limited to, viral infection, bacterial infection, and the like.

To reduce false positive alterations that typically arise in amplification process, the barcode sequences used in the method as described herein can be used to form subgroups of sequences and to arrive at consensus sequences that are then used for further analysis or determination of whether mutation is truly present in the target DNA fragments. Thus, in some examples, step n further comprises:

grouping the sequencing results wherein the barcode sequences are identical, into a subgroup;

comparing the sequencing results within the subgroup thereby determining a consensus sequence;

mapping the consensus sequence to a reference sequence; and identifying differences between the consensus sequence and the reference sequence to analyse and determine whether mutation is truly present in the target DNA fragments.

In one example, the mutation may be single nucleotide variations. In another example, the mutation may be small INDELs. In another example, the mutation may be microsatellite instability.

As used herein, the term "reference sequence" refers to nucleotide sequences (such as DNA sequences or RNA sequences) known in the art that may be obtainable from public databases.

As used herein, the term "consensus sequence" refers to a nucleotide sequence obtained from consensus calling. In one example, consensus calling is performed by identifying the nucleotide at each position for each sequencing result within the subgroup, comparing the identity for the nucleotide at each position across the plurality of sequencing results, and determining a majority nucleotide at each position. If the majority nucleotide count is above a threshold set for determining majority for specific position, the assignment for said position is the majority nucleotide. If the majority nucleotide count is below this threshold, no assignment is made for said position. The threshold is variable for every position and is a function of the total number of sequencing results corresponding to a specific position.

In some examples, the length of the target-specific sequence A, the target-specific sequence B, and/or the target-specific sequence C is from 17 nucleotides to 31 nucleotides, or from 19 nucleotides to 29 nucleotides, or from 20 nucleotides to 28 nucleotides, or from 21 nucleotides to 27 nucleotides, or from 22 nucleotides to 26 nucleotides, or 18 nucleotides, or 19 nucleotides, or 20 nucleotides, or 21 nucleotides, or 22 nucleotides, or 23 nucleotides, or 24 nucleotides, or 25 nucleotides, or 26 nucleotides, or 27 nucleotides, or 28 nucleotides, or 29 nucleotides, or 30 nucleotides. In some examples, the length of the target-specific sequence A, the target-specific sequence B, and/or the target-specific sequence C is 22 nucleotides. A person skilled in the art is also aware that in order to determine the length of the primer A, the primer B, the primer C, the target-specific sequence A, the target-specific sequence B, and/or the target-specific sequence C, he will have to also consider other primer properties including, but not limited to, melting temperature (or Tm), GC-content (or guanine-cytosine content or GC %) and propensity of a primer to dimerize with other primers and itself.

As used herein, a "separation molecule" refers to a tag or molecule that is capable of binding to a bead to thereby allow for the separation of the nucleotide that is connected to the separation molecule. As illustrated in FIG. 1*b* or FIG. 1*d*, the separation molecule may be, but is not limited to biotin, digoxigenin (DIG), Fluorescein isothiocyanate (FITC), and the like. In some examples, the separation molecule is biotin. In consequence, to capture the separation molecule, the bead that binds to the separation molecule may comprise, but is not limited to a substrate linked with streptavidin, anti-digoxigenin, anti-FITC, and the like. In one example, the bead that binds to the separation molecule comprises magnetic beads linked to streptavidin. In some examples, the bead that binds to the separation molecule may be magnetic beads that have been functionalized with streptavidin, anti-digoxigenin, anti-FITC, and the like.

In addition, the method as described herein is compatible with multiple sources of DNA material, including circulating DNA from blood plasma or cerebrospinal fluid (CSF), fragmented formalin-fixed paraffin embedded DNA (FFPE DNA), genomic DNA from leukocytes and from other cells. The method as described herein could also cover more than 50 targeted genes, over 500 targeted regions in the human genome and 15 DNA virus families, and is readily expandable for future inclusion of target regions. As the sequencing library is based on the use of primers for the capture of target regions, it works with equivalent specifications on multiple sample types such as circulating DNA and FFPE DNA. For example, primer-based capture of FFPE DNA is not hindered by fragmentation, as long as the expected amplicon size as defined by primers is limited to a reasonably short length of about 160-bp. Up to eight classes of target regions such as single-nucleotide variations or fusions can also be simultaneously captured using the first set of primers from a single sample of DNA. Following the primer-based capture, steps are taken for the completion of amplicons or ends with sequencing adapters and final amplification before high-throughput sequencing. The combination of primer and PCR-based methods for sequencing analysis allows for a smaller input DNA to be worked with without losing sensitivity. As such, the inventors of the present disclosure envisaged that the method as described herein can be performed in a liquid sample or tissue sample. Thus, in some examples, the sample is a liquid sample, a tissue sample, or a cell sample.

In some examples, the liquid sample may include, but is not limited to, bodily fluids such as, but is not limited to, blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice, pancreatic juice, and the like. In one example, the bodily fluid is blood. The liquid sample that is useful for the method of the present technology is a liquid that comprises DNA which is circulating and not contained within cells (or cell free DNA). The DNA within the liquid can be isolated from the liquid in a form that is free from impurities (or pure form).

In some examples, the tissue sample may include, but is not limited to frozen tissue sample, fixed tissue sample (such as formalin-fixed tissue sample).

The method of the present invention is optimized for DNA fragments having certain sizes. A person skilled in the art is aware that when the DNA sample comprises full-length DNA, the full-length DNA can be processed and fragmented to certain length that is suitable for the method of the present invention. In some examples, the length of the DNA fragment A and/or the DNA fragment B is from 80 base pairs to 220 base pairs, or from 90 base pairs to 210 base pairs, or from 100 base pairs to 200 base pairs, or from 110 base pairs to 190 base pairs, or from 120 base pairs to 180 base pairs, or from 130 base pairs to 170 base pairs, or from 140 base pairs to 160 base pairs, or about 80 base pairs, or about 90 base pairs, or about 100 base pairs, or about 110 base pairs, or about 120 base pairs, or about 130 base pairs, or about 140 base pairs, or about 150 base pairs, or about 160 base pairs, or about 170 base pairs, or about 180 base pairs, or about 190 base pairs, or about 200 base pairs, or about 210 base pairs, or about 220 base pairs. In one example, the length of the DNA fragment A and/or the DNA fragment B is about 150 base pairs.

Since primers are used to detect target defined or undefined regions, the inventors found the method as described herein to be useful in detecting small DNA sample. Thus, in some examples, the amount of DNA sample may be from 10 ng to 200 ng, or from 20 ng to 190 ng, or from 30 ng to 180 ng, or from 40 ng to 170 ng, or from 50 ng to 160 ng, or from 60 ng to 150 ng, or from 70 ng to 140 ng, or from 80 ng to 130 ng, or from 90 ng to 120 ng, or from 100 ng to 110 ng, or about 10 ng, or about 20 ng, or about 30 ng, or about 40 ng, or about 50 ng, or about 60 ng, or about 70 ng, or about 80 ng, or about 90 ng, or about 100 ng, or about 110 ng, or about 120 ng, or about 130 ng, or about 140 ng, or about 150 ng, or about 160 ng, or about 170 ng, or about 180 ng, or about 190 ng, or about 200 ng. In some examples, the amount of DNA sample is about 100 ng.

Since the method as described herein can be used to detect undefined region that comprises structural variations that are not previously characterized, the DNA sample to be used in the method as described herein may include, but is not limited to, a eukaryotic DNA sample, a prokaryotic DNA sample, a viral DNA sample, and a mixture thereof. In some examples, the prokaryotic DNA sample is a bacterial DNA sample. In some examples, the eukaryotic DNA sample may include, but is not limited to, a protozoa DNA sample, a fungal DNA sample, an algae DNA sample, a plant DNA sample, an animal DNA sample, and the like. In some examples, the animal DNA sample is a mammalian DNA sample (such as human DNA sample). In some examples, the DNA sample may be a cell free DNA or DNA of a lysed cell.

In another aspect, the present invention provides for a kit comprising a plurality of primer A as defined herein, a plurality of primer B as defined herein, a plurality of primer C as defined herein, a bead that binds the separation molecule as defined herein, and a double stranded oligonucleotide as defined herein. In some examples, the kit of the present invention further comprises a DNA polymerase, a Taq polymerase, a ligase, a plurality of deoxyribonucleotide triphosphate (dNTPs). In some examples, the reagents provided in the kit as described herein may be provided in separate containers comprising the components independently distributed in one or more containers. As the method as described herein relates to sequencing (such as high-throughput sequencing), further components required in sequencing processes could be easily determined by the person skilled in the art.

As used in this application, the singular form "a," "an," and "the" include plural references unless the context clearly dictates otherwise. For example, the term "a primer" includes a plurality of primers, including mixtures and combinations thereof.

As used herein, the terms "increase" and "decrease" refer to the relative alteration of a chosen trait or characteristic in a subset of a population in comparison to the same trait or characteristic as present in the whole population. An increase thus indicates a change on a positive scale, whereas a decrease indicates a change on a negative scale. The term "change", as used herein, also refers to the difference between a chosen trait or characteristic of an isolated population subset in comparison to the same trait or characteristic in the population as a whole. However, this term is without valuation of the difference seen.

As used herein, the term "about" in the context of concentration of a substance, size of a substance, length of time, or other stated values means +/−5% of the stated value, or +/−4% of the stated value, or +/−3% of the stated value, or +/−2% of the stated value, or +/−1% of the stated value, or +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

EXAMPLES

Material

Exemplary Molecular Tag Complex or Primers when Target is EGFR-exon18_1

An example of a "primer" when the target sequence is EGFR-exon 18 1 (an example of primer A, illustrated in FIG. 1*a*) is as follows:

(SEQ ID NO: 6)

*ACACGACGCTCTTCCGATCT*NNNNNNNNNNGGTGACCCTTGTCTCTGT

GTTC, wherein the bases in italic and underline are an example of adapter sequence, the bases in bold represent the barcode sequence and the bases in underline is an example of target specific sequence.

An example of subsequent primers for the "completion of amplicon" (an example of primer C, illustrated in FIG. 1*c*) is as follows:

(SEQ ID NO: 7)

GACGTGTGCTCTTCCGATCTGAGCCCAGCACTTTGATCTTTTT, where bases in underline are target-specific primers.

Expected amplicon (only target-specific region)

>chr7:55173886 + 55174018 133 bp (SEQ ID NO: 8)

GGTGACCCTTGTCTCTGTGTTCGAGCCCAGCACTTTGATCTTTTTGGTG

ACCCTTGTCTCTGTGTTCttgtcccccccagcttgtggagcctatacac ccagtggagaagacccaaccaagactcttgaggatcttgaaggaaactg aattcAAAAAGATCAAAGTGCTGGGCTC Product after amplicon completion (in two steps) (Only one strand of the double stranded product is shown):

(SEQ ID NO: 9)

ACACGACGCTCTTCCGATCTNNNNNNNNNNGGTGACCCTTGTCTCTGTG

TTCttgtcccccccagcttgtggagcctcttacacccagtggagaagct cccaaccaagctctcttgaggatcttgaaggaaactgaattcAAAAAGA

TCAAAGTGCTGGGCTCAGATCGGAAGAGCACACGTC, where the bases in underline is target nucleic acid.

Universal amplification primer 1 (an example of the primer for amplifying product C or D):

(SEQ ID NO: 10)

AATGATACGGCGACCACCGAGATCTACACTCTTTCCCTACACGACGCTCT

TCCGATC*T

Universal amplification primer 2 (indexed) (an example of the primer for amplifying product C or D, the index is the bases in bold and italic font):

(SEQ ID NO: 11)

CAAGCAGAAGACGGCATACGAG*ATATCACG*GTGACTGGAGTTCAGACGT

GTGCTCTTCCGATC*T

Final Product (Suitable for Sequencing on Illumina)

(SEQ ID NO: 12)

AATGATACGGCGACCACCGAGATCTACACTCTTTCCCTACACGACGCTCT

TCCGATCTNNNNNNNNNNGGTGACCCTTGTCTCTGTGTTCttgtcccccc cagcttgtggagcctcttacacccagtggagaagctcccaaccaagctct cttgaggatcttgaaggaaactgaattcAAAAAGATCAAAGTGCTGGGCT

CAGATCGGAAGAGCACACGTCTGAACTCCAGTCACCGTGATATCTCGTAT

GCCGTCTTCTGCTTG, where the bases in underline is target nucleic acid.

Methods

DNA Library Generation

The workflow for preparing DNA library is divided into three major steps. In the first step (FIG. 1*a*), target DNA were captured using a multiplex pool of primers. Each primer is a molecular tag complex comprising an oligonucleotide with 10 random nucleotides (a molecular tag/barcode sequence) linked to a target-specific primer, which functions in target capture. Some of the primers in primer pool for target capture are 5' biotin-labeled (B). An example of the primer that is biotin-labeled is shown on FIG. 5.

Briefly, in a 50 μl reaction, 10-100 ng of DNA was mixed with a primer pool in which each primer was at 0.05-0.2 μM, 0.2 mM of dNTPs, 0.5-1.5 nM $MgSO_4$, 0.6 units of KOD enzyme and reaction buffer. Target capture and enrichment was done using the following thermocycling conditions: Denaturation at 94° C. for 1 min, followed by 1 to 3 cycles of 98° C. for 1 min, 60° to 65° C. for 6 mins, and 68° C. for 5 mins. The length of the targets captured was dictated by the length of the template DNA fragment, and the extension time allowed, such that a variety of target lengths would be captured in this first step. Three cycles were allowed to compensate for less than 100% efficiency of primer binding to targets, so as to increase target capture. At the end of this reaction, each captured target DNA had a random molecular tag linked to it. Excess unused primers were removed by purification with 1.5× AMPure XP beads in two rounds. This means eluate from the first round of purification was bound to 1.5× beads and subjected to a second round of purification. Final elution was done in 10 to 30 μl of buffer EB.

Product after Step 1 (Examples of Product a and Complex B, Illustrated in FIG. 1*b*):

An example with a very short target captured region shown for illustrative purposes is shown on FIG. 6.

In the second step (FIGS. 1*b*-1*e*), targets with defined (specified) ends and those with undefined ends were subjected to distinct treatments to complete the structure of a target-specific amplicon which could then be amplified to generate a sequencing platform-specific DNA library molecule. Before this could be done, targets with undefined ends were separated from other targets using the biotin tags incorporated in the target capture primers. Briefly, the 10 to 30 μl eluate from step 1 (target capture) was mixed with an equal volume of washed MyOne Streptavidin C1 beads, and the bead mix was allowed to incubate at room temperature with intermittent mixing for 1 hour to allow the binding of biotin to streptavidin. With this step, target DNA that were captured with biotin-labeled primers become immobilized on the streptavidin-coated beads. Meanwhile, target DNA captured with unlabeled primers remain in the supernatant (or bead solution mix). At the end of one hour, the supernatant containing target DNA captured with unlabeled primers were collected separately, and the target DNA captured with biotin-labeled primers were on beads, thus achieving separation of captured DNA intended for different treatments in step 2 for amplicon-generation.

Targets captured on beads were washed briefly with bead wash (B&W) solution, followed by "on-bead" A-tailing reaction. Briefly, the beads with immobilized targets were resuspended in 10 μl reaction mixture containing 6.4 μl water, 1 μl 10× buffer for KOD-Plus-Neo, 1 μl of 2 mM dNTPs, 0.6 μl of 25 mM $MgSO_4$, and 1 μl of 10× A-attachment mix (Toyobo Co., Ltd., Japan). The beads were incubated at 60° C. for 10 mins to allow A-tailing of the captured, immobilized DNA targets. The beads were washed again with 1× B&W buffer. Following this, the beads were resuspended in a ligation mix to allow "on-bead" ligation of a ds-oligo partial adapter. Briefly, beads were resuspended in a 10 μl reaction mix containing 5 μl of Blunt/TA ligase master mix (NEB, USA), 4 μl of water, and 1 μl of 10 μM adapter with a 3' T overhang. An example of a 3' T overhang is shown for example on FIG. 7 (the 3' T overhang is bolded and underlined).

The mixture was incubated at 25° C. for 1 hr, with intermittent shaking. At the end of hours, the mixture was chilled on ice. The beads were then washed three times with 1× B&W buffer. At the end of this step, target DNA captured on the beads would have undergone amplicon-generation by the one-sided ligation of the partial adapter. Adapter ligation on the other (immobilized) end was inhibited due to the overhang tail introduced during target capture, and the presence of biotin-streptavidin complex. Finally, the completed amplicons were eluted from the streptavidin beads by disrupting the biotin-streptavidin bonds, by incubating the beads in 10 μl of elution solution (10 mM EDTA pH 8.2 and 95% formamide) at 65° C. for 5 mins to elute biotin labelled targets from the beads. The eluate was collected following magnetic separation of streptavidin beads. The eluate containing captured DNA targets (converted to amplicons) was collected and purified once with 1.5× AMPure XP beads to remove the formamide solution and replace it with EB buffer. DNA was eluted in 11.5 μl Buffer EB.

Targets that were not captured on streptavidin beads, as they lacked biotin tags, were first purified once with 1.5× AMPure XP beads to replace the B&W buffer with sample buffer. DNA was eluted in 23 μl of Buffer EB. Amplicon-generation was then done using a multiplex pool of "reverse" target-specific primers. Briefly, in a 50 μl reaction, purified DNA from target capture step is mixed with a primer pool in which each primer is at 0.05-0.2 μM, 0.5-1.5 mM of dNTPs, 1.5 nM $MgSO_4$, 1 unit of KOD enzyme and reaction buffer. Amplicon generation was done using the following thermocycling conditions: Denaturation at 94° C. for 1 min, followed by 1 to 3 cycles of 98° C. for 1 min, 60° C. for 6 mins, and 68° C. for 5 mins. The completed amplicons were purified twice from the PCR mix with 1.5× AMPure beads. DNA was eluted in 11.5 μl Buffer EB. An example of the product after step 2 if target captured goes through adapter ligation for amplicon generation is shown on FIG. 8*a* and an example of the product after step 2 if target captured is converted to amplicon with a second primer is shown on FIG. 8*b*.

In the third step (FIG. 1*f*), a final amplification was performed to amplify the targets and to complete the library structure required for sequencing on the Illumina platform, by introducing sequencing adapters. Briefly, the purified targets (amplicons from step 2), both with defined (specified) ends and those with undefined (unknown) ends from the starting DNA material are recombined and pooled into one final PCR reaction. Briefly, 23 μl of combined DNA (11.5 μl from each procedure for biotin-labeled and unlabeled targets) is mixed with 1 μl of 5-20 μM universal P5 adapter (AATGATACGGCGACCACCGAGATCTACACTCTTTCCCTACACGACGCTC
TTCCGATCT, P5 sequence is underlined), 1 μl of 5-20 UM indexed P7 adapter (Table 1) and KAPA HiFi HotStart ReadyMix in a 50 μl reaction. The PCR was carried out with the following profile: Denaturation at 98° C. for 45 s, followed by 22-26 cycles of 98° C. for 15 s, 60° C. for 30 s, and 72° C. for 30 s, with a final extension at 72° C. for 1 min. The amplified library was purified twice with 0.6-0.8× AMPure XP beads to remove non-specific products. The quality and quantity of the sequencing library was assessed using the 4200 Tapestation system (Agilent Technologies, USA) and KAPA Library Quantification Kit for Illumina® Platforms (Kapa Biosystems Inc., USA) respectively. An Example of the product after step 3 is shown on FIG. 9.

Libraries were multiplexed and paired-end sequencing (2×150 bp) was done following manufacturer's instructions.

Molecular tag (or barcode) sequences were included in the trimmed "primer" sequences of Read 1, and could be extracted given the unique structure of primer sequences in Read 1. The extracted molecular tag sequences are clustered in two steps: 1. Initial grouping by exact match of the combination of amplicon_name+barcode sequence and 2. Cluster Reassignment, in each group of same amplicon_name, barcodes were further reassigned using global pairwise alignment with maximum 2 base differences between barcodes. Barcode clusters with number of associated reads less than 3 (after cluster reassignment) were considered unreliable clusters and removed from downstream analysis.

TABLE 1

| P7 adapter Sequence (P7 adapter sequence is italicized and the sample indexes are in bold underline) | |
|---|---|
| R_ID1 (SEQ ID NO: 15) | *CAAGCAGAAGACGGCATACGAGAT***ATCACG**GTGACTGGAGTTCAGACGTGTGCTCTTCCGATCT |
| R_ID2 (SEQ ID NO: 16) | *CAAGCAGAAGACGGCATACGAGAT***CGATGT**GTGACTGGAGTTCAGACGTGTGCTCTTCCGATCT |
| R_ID3 (SEQ ID NO: 17) | *CAAGCAGAAGACGGCATACGAGAT***TTAGGC**GTGACTGGAGTTCAGACGTGTGCTCTTCCGATCT |
| R_ID4 (SEQ ID NO: 18) | *CAAGCAGAAGACGGCATACGAGAT***TGACCA**GTGACTGGAGTTCAGACGTGTGCTCTTCCGATCT |
| R_ID5 (SEQ ID NO: 19) | *CAAGCAGAAGACGGCATACGAGAT***ACAGTG**GTGACTGGAGTTCAGACGTGTGCTCTTCCGATCT |
| R_ID6 (SEQ ID NO: 20) | *CAAGCAGAAGACGGCATACGAGAT***GCCAAT**GTGACTGGAGTTCAGACGTGTGCTCTTCCGATCT |
| R_ID7 (SEQ ID NO: 21) | *CAAGCAGAAGACGGCATACGAGAT***CAGATC**GTGACTGGAGTTCAGACGTGTGCTCTTCCGATCT |
| R_ID8 (SEQ ID NO: 22) | *CAAGCAGAAGACGGCATACGAGAT***ACTTGA**GTGACTGGAGTTCAGACGTGTGCTCTTCCGATCT |
| R_ID9 (SEQ ID NO: 23) | *CAAGCAGAAGACGGCATACGAGAT***GATCAG**GTGACTGGAGTTCAGACGTGTGCTCTTCCGATCT |
| R_ID10 (SEQ ID NO: 24) | *CAAGCAGAAGACGGCATACGAGAT***TAGCTT**GTGACTGGAGTTCAGACGTGTGCTCTTCCGATCT |
| R_ID11 (SEQ ID NO: 25) | *CAAGCAGAAGACGGCATACGAGAT***GGCTAC**GTGACTGGAGTTCAGACGTGTGCTCTTCCGATCT |
| R_ID12 (SEQ ID NO: 26) | *CAAGCAGAAGACGGCATACGAGAT***CTTGTA**GTGACTGGAGTTCAGACGTGTGCTCTTCCGATCT |
| R_ID13 (SEQ ID NO: 27) | *CAAGCAGAAGACGGCATACGAGAT***AGTCAA**GTGACTGGAGTTCAGACGTGTGCTCTTCCGATCT |
| R_ID14 (SEQ ID NO: 28) | *CAAGCAGAAGACGGCATACGAGAT***AGTTCC**GTGACTGGAGTTCAGACGTGTGCTCTTCCGATCT |

Data Analysis

FASTQ files were processed using a custom pipeline. First, expected amplicons were identified and labeled in the FASTQ files based on the expected primer sequences in Read 1 and paired Read 2. For amplicons with one unknown end, only primers in Read 1 were used for identification and labeling. Primer sequences and upstream molecular tag sequences were trimmed using cutadapt, primer trimmed sequences were mapped to the reference genome using bwa-mem. For "primer" trimmed fastq files, the name of the primer which had the best match to a read was concatenated to the name of the mapped output reads (for both Read 1 and Read 2). The primer name assigned to Read 1 might not always match that of Read 2, which could be due to overlapping amplicons or non-specific binding. An "amplicon_name" was assigned to each paired read by combining the matching primer name of Read 1 and Read 2 (concatenated by semicolon).

Consensus Calling was done for each molecular tag (or barcode) cluster, by first performing global alignment among all associated reads using MAFFT. The consensus base in each aligned position was called by determining the majority representative base type, the percentage of which is no less than an automatically determined threshold. The threshold was a function of the total number of reads for that barcode sequence. If no representative base could be called, the position was assigned N (as opposed to one of A, C, T, G). A new quality score was assigned to each position, which was either $90^{th}$ percentile of all the quality values from the representative base type in that position (if a consensus base was found), or $10^{th}$ percentile of all quality values in that position (if no consensus bases was found). The consensus reads were written to a new FASTQ file. An exemplary result of the consensus reads mapped to the reference is shown on FIG. 3.

The consensus FASTQ files were mapped to the reference genome, with local realignment to improve mapping. Read depth was calculated from the mapped BAM file in the target regions in the specified .bed file (of expected amplicons or regions). Variant calling was performed on consensus BAM files using Mutect2, lofreq and a custom variant caller. Exemplary result of the library generation is shown on FIG. 2.

Exemplary results for variant detection and frequency of clinical samples are shown on Table 2 (FIGS. 15*a*-15*b*) and exemplary results for detection of Epstein Barr Virus (EBV) microbial DNA targets in clinical samples are shown on Table 3 (FIGS. 16*a*-16*e*). To generate the results in Table 2 and Table 3, clinical samples which have been previously characterized for EGFR mutations (positive or negative) and EBV DNA (present or absent) by orthogonal methods (such as Quantitative PCR) were identified. Cell-free DNA (cfDNA) was extracted from the same samples which had been selected to have had sufficient plasma. The extracted cfDNA was quantified and processed with the method as described herein to determine if similar results of detection (of EGFR mutations and EBV DNA) with orthogonal methods (such as Quantitative PCR) could be achieved. Tables 2 and 3 summarize the findings of orthogonal methods (such as Quantitative PCR) presented together with findings from the method as described herein. As can be seen in Table 2, 16 clinical samples (plasma) were tested by the method as described herein and by quantitative PCR, respectively, for detection of EGFR mutations (such as small nucleotide variants, and small INDELs) and determination of the frequency of mutations. The result showed 98% concordance of mutation detection and agreement of mutant allele frequency by both methods. The sample numbers in the first column of Table 2 which showed concordance between the conventional method (quantitative PCR) and the method of the present invention are: 1, 2, 3, 4, 5 (for L858R), 6, 7, 8, 9, 10, 11 (for EGFR c.2236_2250del), 12, 13, 14, 15 (for E746_A750delELRA and EGFR T790M), and 16 (for KRAS G12D). In addition, in contrast to quantitative PCR, which is used to detect various mutations in separate reactions (each reaction is used to detect one mutation, i.e. each row in column 2 (labeled "Mutation reported by AS-PCR") of Table 2 corresponds to one single reaction), the method of present invention is able to simultaneously detect multiple mutations in the same sample, in one single reaction (i.e. all the mutations listed in all the rows in column 6 (labeled "Variant identified by Hallmark") of Table 2 are detected in one single reaction). As can be seen in Table 3, detection of Epstein Barr Virus (EBV) microbial DNA targets BamHI-W and EBNA1, in clinical samples (plasma) by the method as described herein and quantitative PCR showed 89% concordance of detection. The sample numbers in the first column of Table 3 which showed concordance between the conventional method (quantitative PCR) and the method of the present invention are: 17, 19, 20, 21, 22, 23, 24, 25, 26, 27, 28, 29, 30, 32, 33, 34 and 35. Additionally, mutations in human DNA were detected. Also, in serial samples from the same individual, matched mutations (such as small nucleotide variants, and small INDELs) were present. Serial samples from the same individual are depicted within a black box and are shaded in grey. Thus, the method of the present inventions is able to simultaneously detect viral DNA and mutations in human DNA. In addition, in contrast to quantitative PCR, which is used to detect various mutations and the viral DNA in separate reactions (each reaction is used to detect one mutation or viral DNA, i.e. each row in column 2 (labeled "EBV BamHI-W") of Table 3 corresponds to one single reaction), the method of present invention is able to simultaneously detect multiple mutations in human DNA and the viral DNA in the same sample, in one single reaction (i.e. all the mutations listed in all the rows in column 11 (labeled "Mutations") of Table 3 are detected in one single reaction). Exemplary result for the summary of Variant allele frequency (VAF) observed using the method of the present invention vs. standards is shown on FIG. 4.

Exemplary use of the sequencing results obtained using the method of the present invention for the detection of fusion is shown in FIG. 10. The process for detection of fusion as shown in FIG. 10 is described as follows:

(1) A sample was obtained from cell line DNA with known structural variations, for the purpose of validating the method of the present invention. The DNA was fragmented to generate fragments with sizes ranging from 20-400 bp;

(2) The fragmented DNA (100 ng) underwent conversion to sequencing library as described in the methods. An appropriate primer pool was used in the initial target capture such that primers for the capture of a broad region of ROS1 known to undergo structural variations were included in the target capture;

(3) Sequencing and data analysis was performed according to the methods described in the section of "Data Analysis" above;

(4) Mapped reads were inspected in Integrated genome Viewer (IGV) for the presence of a) soft-clip, b) insertions and/or 3) mapping of Reads 1 and 2 of a paired sequencing read to physically separated regions of the genome. Two or more such supporting paired reads carrying the breakpoint or mapping to distant regions of genome were required to support the call for structural variant. The "partner" of the structural variant was identified by the mate read location or by aligning (BLASTing) an insertion or soft-clip sequence against the human genome to identify the origin of the insertion sequence.

The above process may be used for detecting structural variation in any target region known to undergo structural variation without prior knowledge of the precise location of the breakpoint. The above process may also be applied to DNA from fixed tissue (which is already fragmented to varying degrees) or cfDNA from plasma, pleural fluid or cerebrospinal fluid.

In addition, examples of other types of structural variants which may be detected using the above mentioned process are:

Inversion

An example of detection of a structural variant described as an inversion, in which a DNA sequence is reversed end to end, is shown in FIG. 11(*a*) at the level of a chromosome.

The resulting inversion in a smaller target region of interest is represented in FIG. 11(*b*), with sequence directionality indicated by arrows in wild-type condition and in the condition with the inversion. The inversion may involve a large part of the genome or a relatively small part resulting in two breakpoints.

An example of an inversion involving a region of chromosome 9 with breakpoints determined at exactly chr9:5,467,953 and chr9:6,557,405, was detected by the method of the invention (FIG. 12). The inversion shown in FIG. 12 is one which results in a portion of genome from chr9:6,557,405 to become adjacent in inverted form to chr9: chr9:5, 467,953. FIG. 12 depicts paired reads from sequencing results, Reads 1 and 2, which map to different non-contiguous locations of the genome, as derived from the mapping of the reads sequence.

Translocation

An example of a translocation involving a region of chromosome 6 and chromosome 4 is shown in FIG. 13. Breakpoints are deducible from sequencing results obtained by the method of the invention. FIG. 14 depicts paired reads from sequencing results, Reads 1 and 2, which map to different non-contiguous locations of the genome, as derived from the mapping of the reads sequence.

In principle, any of the following listed types of other structural variants:

duplication;

insertion;

transversion;

are detectable by the method of the invention, as long as a breakpoint in a target region of interest is captured among the sequencing reads. The non-contiguous nature of the alignment of the sequencing read allows for the detection of any form of structural variant. In other words, as long as the method of the invention incorporates capture primers/probes for a target region of interest known to undergo any one of the structural variations mentioned above, that type of structural variant can be detected. This is because, once sequencing reads are available, detection of structural variants may be done by the alignment of the reads to two different non-contiguous parts of the genome. Based on the method of the invention, it is not critical that the non-contiguous part of the read comes from the same chromosome and is inverted (i.e. inversion) or from another chromosome (i.e. translocation).

Comparison of the Method of the Invention to Conventional Methods

Compared to conventional methods of next-generation sequencing using hybridization capture of targets or primer-based amplicon capture, the performance of the method of the invention is comparable to the conventional methods for detection of various types of genomic alterations, as established during the development and validation phase of the method (please refer to Tables 2 and 3). As can be seen in Table 4 below, the method of the invention achieved more than 99% sensitivity and specificity for detecting small nucleotide variations (SNVs) at all the mutant allele frequency tested; more than >83.3% sensitivity and specificity for detecting INDELs at 0.1% mutant allele frequency and more than 99% sensitivity and specificity for detecting INDELs at 1%, 5% and 10% mutant allele frequency tested; more than >50% sensitivity and specificity for detecting fusions at 1% mutant allele frequency and more than 99% sensitivity and specificity for detecting fusions at 5% and 10% mutant allele frequency tested. In addition, the various mutations listed in FIG. 4 are detected by the method of the present invention simultaneously, in one single reaction.

TABLE 4

Sensitivity and specificity of the method of the invention for the detection of various kinds of mutations.

| | | MUTANT ALLELE FREQUENCY | | | | | | | |
|---|---|---|---|---|---|---|---|---|---|
| | | 0.1% | | 1% | | 5% | | 10% | |
| | | Sensitivity | Specificity | Sensitivity | Specificity | Sensitivity | Specificity | Sensitivity | Specificity |
| Mutation Class | SNVs | >99% | >99% | >99% | >99% | >99% | >99% | >99% | >99% |
| | INDELs | >83.3% | >99% | >99% | >99% | >99% | >99% | >99% | >99% |
| | Fusions | | — | >50% | >99% | >90% | >99% | >90% | >99% |

In addition, compared to the conventional methods, the method of the invention possesses unexpected advantages. For example, the method of the invention is able to achieve simultaneous detection of: 1) Viral DNA; 2) Microsatellite instability; 3) Structural rearrangements; 4) SNVs and IND ELs from samples ranging from cfDNA from plasma (or cerebrospinal fluid, pleural effusion) or DNA from fixed tissue.

Compared to the method of the invention, conventional methods do not allow for the simultaneous detection of these genomic alteration types or are not amenable to function with multiples sources of DNA.

The invention claimed is:

1. A method of simultaneously capturing and identifying distinct targets within a nucleic acid sample, wherein the distinct targets comprise a defined target region and a variant of the defined target region, wherein the variant of the defined target region comprises structural variations or rearrangement or fusion, comprising the steps of:

a) providing a main mixture comprising a plurality of nucleic acid fragments A, a plurality of nucleic acid fragments B, a polymerase, a single-stranded primer A, and a single-stranded primer B, wherein:
   the nucleic acid fragment A is a nucleic acid fragment comprising a part of the defined target region;
   the nucleic acid fragment B is a nucleic acid fragment comprising a part of the variant of the defined target region;
   the primer A comprises a barcode sequence and a target-specific sequence A,
   wherein the target-specific sequence A is an oligonucleotide complementary to a sequence at/close to the 3' end of a strand of the nucleic acid fragment A; and
   the primer B comprises a separation molecule, a barcode sequence, and a target-specific sequence B,
   wherein the target-specific sequence B is an oligonucleotide complementary to a sequence within a strand of nucleic acid fragment B, b) annealing the primer A to the nucleic acid fragment A and the primer B to the nucleic acid fragment B;

c) allowing the polymerase to elongate the primer A and the primer B thereby obtaining a double stranded product A and a double stranded product B, wherein:
   the double stranded product A is a single stranded elongated primer A that is annealed to the nucleic acid fragment A; and
   the double stranded product B is a single stranded elongated primer B that is annealed to the nucleic acid fragment B;

d) adding a bead that binds the separation molecule in the main mixture and allowing the separation molecule in the double stranded product B to bind to the bead thereby forming a double stranded complex B;

e) separating the double stranded product A and the double stranded complex B in the main mixture thereby obtaining a mixture A and a mixture B, wherein:
   the mixture A comprises the double stranded product A and
   the mixture B comprises the double stranded complex B;

f) adding a primer C to the mixture A, wherein the primer C comprises a target-specific sequence C,
   wherein the target-specific sequence C is an oligonucleotide complementary to a sequence at/close to the 3' end of the single stranded elongated primer A;

g) denaturing the double stranded product A in the mixture A thereby allowing the primer C to anneal to the single stranded elongated primer A;

h) allowing the polymerase to elongate the primer C thereby obtaining a double stranded product C, wherein the double stranded product C is a single stranded elongated primer C that is annealed to the single stranded elongated primer A;

i) connecting a single nucleotide to the 3' end of the single stranded elongated primer B of the double stranded complex B in the mixture B;

j) adding a double stranded oligonucleotide to the mixture B wherein the double stranded oligonucleotide comprises a nucleotide overhang complementary to the single nucleotide of step i);

k) ligating the double stranded oligonucleotide to double stranded complex B at the 3' end of the single stranded elongated primer B and 5' end of the nucleic acid fragment B thereby obtaining a double stranded product D;

l) combining the double stranded product C and the double stranded product D;

m) amplifying the double stranded product C and the double stranded product D thereby obtaining a plurality of amplicons;

n) sequencing the plurality of amplicons thereby obtaining a plurality of sequencing results;

o) using the plurality of sequencing results for:
   identifying single nucleotide sequence variations, or small insertions, or small deletions, or copy number alteration, or deletions of homopolymeric regions, or polymorphism, or microsatellite instability within the defined target regions, and/or
   identifying the structural variations within the variant of the defined target regions, or
   quantifying the number of distinct targets within the nucleic acid sample.

2. The method of claim 1, wherein the barcode sequence of primer A and primer B is an oligonucleotide comprising 10 to 16 random nucleotides, or 10 to 15 random nucleotides, or 10 to 13 random nucleotides, or 10 random nucleotides, or 11 random nucleotides, or 12 random nucleotides, or 13 random nucleotides, or 14 random nucleotides, or 15 random nucleotides, or 16 random nucleotides.

3. The method of claim 1, wherein the barcode sequence of primer A and primer Bis an oligonucleotide comprising 10 random nucleotides.

4. The method of claim 1, wherein the primer A, the primer B, the primer C and/or the double stranded oligonucleotide further comprises an adapter sequence.

5. The method of claim 1, wherein the structural variation is selected from the group consisting of deletion, duplication, insertion, inversion, transversion, and translocation.

6. The method of claim 1, wherein the plurality of sequencing results are further used to detect a point mutation within the variant of the defined target regions.

7. The method of claim 1, wherein step o) further comprises:

a) grouping the sequencing results wherein the barcodes are identical into a subgroup;

b) comparing the sequencing results within the subgroup thereby determining a consensus sequence;

c) mapping the consensus sequence to a reference sequence; and d) identifying differences between the consensus sequence and the reference sequence.

8. The method of claim 1, wherein the length of the target-specific sequence A, the target-specific sequence B, and/or the target-specific sequence C is from 17 nucleotides to 31 nucleotides, or from 19 nucleotides to 29 nucleotides, or from 20 nucleotides to 28 nucleotides, or from 21 nucleotides to 27 nucleotides, or from 22 nucleotides to 26 nucleotides, or 16 nucleotides, or 17 nucleotides, or 18 nucleotides, or 19 nucleotides, or 20 nucleotides, or 21 nucleotides, or 22 nucleotides, or 23 nucleotides, or 24 nucleotides, or 25 nucleotides, or 26 nucleotides, or 27 nucleotides, or 28 nucleotides, or 29 nucleotides, or 30 nucleotides.

9. The method of claim 1, wherein the separation molecule is selected from the group consisting of biotin, digoxigenin (DIG), and Fluorescein isothiocyanate (FITC).

10. The method of claim 1, wherein the separation molecule is biotin.

11. The method of claim 1, wherein the bead that binds the separation molecule comprises streptavidin, anti-digoxigenin, or anti-FITC.

12. The method of claim 1, wherein the bead that binds the separation molecule comprises streptavidin.

13. The method of claim 1, wherein the nucleic acid sample is obtained from a subject having and/or suspected of having a disease.

14. The method of claim 13, wherein the disease is a cancer selected from the group consisting of lung cancer, colorectal cancer, breast cancer, pancreatic cancer, prostate cancer, nasopharyngeal cancer, liver cancer, cholangiocarcinoma, esophageal cancer, urothelial cancer, and gastrointestinal cancer.

15. The method of claim 13, wherein the disease is an infectious disease selected from a viral infection and a bacterial infection.

16. The method of claim 1, wherein the nucleic acid sample is a liquid sample, a tissue sample, or a cell sample.

17. The method of claim 16, wherein the liquid sample is bodily fluids selected from the group consisting of blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice, and pancreatic juice.

18. The method of claim 17, wherein the bodily fluid is blood.

19. The method of claim 16, wherein the tissue sample is a frozen tissue sample or a fixed tissue sample.

20. The method of claim 1, wherein the length of the nucleic acid fragment A and/or the nucleic acid fragment B is from 80 nucleotides to 220 nucleotides, or from 90 nucleotides to 210 nucleotides, or from 100 nucleotides to 200 nucleotides, or from 110 nucleotides to 190 nucleotides, or from 120 nucleotides to 180 nucleotides, or from 130 nucleotides to 170 nucleotides, or from 140 nucleotides to 160 nucleotides, or about 80 nucleotides, or about 90 nucleotides, or about 100 nucleotides, or about 110 nucleotides, or about 120 nucleotides, or about 130 nucleotides, or about 140 nucleotides, or about 150 nucleotides, or about 160 nucleotides, or about 170 nucleotides, or about 180 nucleotides, or about 190 nucleotides, or about 200 nucleotides, or about 210 nucleotides, or about 220 nucleotides.

21. The method of claim 1, wherein the length of the nucleic acid fragment A and/or the nucleic acid fragment B is about 150 nucleotides.

22. The method of claim 1, wherein the amount of nucleic acid sample is from 10 ng to 200 ng, or from 20 ng to 190 ng, or from 30 ng to 180 ng, or from 40 ng to 170 ng, or from 50 ng to 160 ng, or from 60 ng to 150 ng, or from 70 ng to 140 ng, or from 80 ng to 130 ng, or from 90 ng to 120 ng, or from 100 ng to 110 ng, or about 10 ng, or about 20 ng, or about 30 ng, or about 40 ng, or about 50 ng, or about 60 ng, or about 70 ng, or about 80 ng, or about 90 ng, or about 100 ng, or about 110 ng, or about 120 ng, or about 130 ng, or about 140 ng, or about 150 ng, or about 160 ng, or about 170 ng, or about 180 ng, or about 190 ng, or about 200 ng.

23. The method of claim 1, wherein the amount of nucleic acid sample is about 100 ng.

24. The method of claim 1, wherein the nucleic acid sample is selected from the group consisting of a eukaryotic nucleic acid sample, a prokaryotic nucleic acid sample, a viral nucleic acid sample, and a mixture thereof.

25. The method of claim 1, wherein the prokaryotic nucleic acid sample is a bacterial nucleic acid sample.

26. The method of claim 1, wherein the eukaryotic nucleic acid sample is selected from the group consisting of a protozoa nucleic acid sample, a fungal nucleic acid sample, an algae nucleic acid sample, a plant nucleic acid sample, and an animal nucleic acid sample.

27. The method of claim 26, wherein the animal nucleic acid sample is a mammalian nucleic acid sample.

28. The method of claim 27, wherein the mammalian nucleic acid sample is a human nucleic acid sample.

29. The method of claim 1, wherein the nucleic acid sample is a cell free nucleic acid or nucleic acid of a lysed cell.

30. The method according to claim 1, wherein the nucleic acid sample is a DNA sample.

* * * * *

SEQUENCE LISTING

```
<160> NUMBER OF SEQ ID NOS: 28

<210> SEQ ID NO 1
<211> LENGTH: 10
<212> TYPE: DNA
<213> ORGANISM: Artificial Sequence
<220> FEATURE:
<223> OTHER INFORMATION: barcode sequence
<220> FEATURE:
<221> NAME/KEY: misc_feature
<222> LOCATION: (1)..(10)
```

<223> OTHER INFORMATION: n is a, c, g, or t

<400> SEQUENCE: 1 nnnnnnnnnn 10

<210> SEQ ID NO 2
<211> LENGTH: 10
<212> TYPE: DNA
<213> ORGANISM: Artificial Sequence
<220> FEATURE:
<223> OTHER INFORMATION: an example of the barcode sequence

<400> SEQUENCE: 2
cattacatac 10

<210> SEQ ID NO 3
<211> LENGTH: 10
<212> TYPE: DNA
<213> ORGANISM: Artificial Sequence
<220> FEATURE:
<223> OTHER INFORMATION: an exemple of the barcode sequence

<400> SEQUENCE: 3
gcgtggacaa 10

<210> SEQ ID NO 4
<211> LENGTH: 10
<212> TYPE: DNA
<213> ORGANISM: Artificial Sequence
<220> FEATURE:
<223> OTHER INFORMATION: an example of the barcode sequence

<400> SEQUENCE: 4
tttttagaca 10

<210> SEQ ID NO 5
<211> LENGTH: 10
<212> TYPE: DNA
<213> ORGANISM: Artificial Sequence
<220> FEATURE:
<223> OTHER INFORMATION: an example of the barcode sequence

<400> SEQUENCE: 5
taagaggtcc 10

<210> SEQ ID NO 6
<211> LENGTH: 52
<212> TYPE: DNA
<213> ORGANISM: Artificial Sequence
<220> FEATURE:
<223> OTHER INFORMATION: an example of a “primer” when the target sequence is EGFR-exon 181 (an example of primer A, illustrated in Figure 1a)
<220> FEATURE:
<221> NAME/KEY: misc_feature
<222> LOCATION: (21)..(30)
<223> OTHER INFORMATION: n is a, c, g, or t

<400> SEQUENCE: 6
acacgacgct cttccgatct nnnnnnnnnn ggtgaccctt gtctctgtgt tc 52

<210> SEQ ID NO 7
<211> LENGTH: 43
<212> TYPE: DNA
<213> ORGANISM: Artificial Sequence
<220> FEATURE:
<223> OTHER INFORMATION: an example of subsequent primers for the "completion of amplicon" (an example of primer C, illustrated in Figure 1c)

<400> SEQUENCE: 7
gacgtgtgct cttccgatct gagcccagca ctttgatctt ttt 43

<210> SEQ ID NO 8
<211> LENGTH: 178
<212> TYPE: DNA
<213> ORGANISM: Artificial Sequence
<220> FEATURE:
<223> OTHER INFORMATION: one example of expected amplicon (only target-specific region)

<400> SEQUENCE: 8
ggtgaccctt gtctctgtgt tcgagcccag cactttgatc tttttggtga cccttgtctc 60
tgtgttcttg tcccccccag cttgtggagc ctcttacacc cagtggagaa gctcccaacc 120
aagctctctt gaggatcttg aaggaaactg aattcaaaaa gatcaaagtg ctgggctc 178

<210> SEQ ID NO 9
<211> LENGTH: 183
<212> TYPE: DNA
<213> ORGANISM: Artificial Sequence
<220> FEATURE:
<223> OTHER INFORMATION: an example of the product after amplicon completion (in two steps) (only one strand of the double stranded product is shown)
<220> FEATURE:
<221> NAME/KEY: misc_feature
<222> LOCATION: (21)..(30)
<223> OTHER INFORMATION: n is a, c, g, or t

<400> SEQUENCE: 9
acacgacgct cttccgatct nnnnnnnnnn ggtgaccctt gtctctgtgt tcttgtcccc 60
cccagcttgt ggagcctctt acacccagtg gagaagctcc caaccaagct ctcttgagga 120
tcttgaagga aactgaattc aaaaagatca aagtgctggg ctcagatcgg aagagcacac 180
gtc 183

<210> SEQ ID NO 10
<211> LENGTH: 58
<212> TYPE: DNA
<213> ORGANISM: Artificial Sequence
<220> FEATURE:
<223> OTHER INFORMATION: Universal amplification primer 1 (an example of the primer for amplifying product C or D)

<400> SEQUENCE: 10
aatgatacgg cgaccaccga gatctacact ctttccctac acgacgctct tccgatct 58

<210> SEQ ID NO 11
<211> LENGTH: 64
<212> TYPE: DNA
<213> ORGANISM: Artificial Sequence
<220> FEATURE:
<223> OTHER INFORMATION: Universal amplification primer 2 (indexed) (an example of the primer for amplifying product C or D, the index is the bases in bold and italic font)

<400> SEQUENCE: 11
caagcagaag acggcatacg agatatcacg gtgactggag ttcagacgtg tgctcttccg 60
atct 64

<210> SEQ ID NO 12

<211> LENGTH: 265
<212> TYPE: DNA
<213> ORGANISM: Artificial Sequence
<220> FEATURE:
<223> OTHER INFORMATION: an example of the final product (suitable for sequencing on Illumina)
<220> FEATURE:
<221> NAME/KEY: misc_feature
<222> LOCATION: (59)..(68)
<223> OTHER INFORMATION: n is a, c, g, or t

<400> SEQUENCE: 12

```
aatgatacgg cgaccaccga gatctacact ctttccctac acgacgctct tccgatctnn     60

nnnnnnnngg tgacccttgt ctctgtgttc ttgtcccccc cagcttgtgg agcctcttac    120

acccagtgga gaagctccca accaagctct cttgaggatc ttgaaggaaa ctgaattcaa    180

aaagatcaaa gtgctgggct cagatcggaa gagcacacgt ctgaactcca gtcaccgtga    240

tatctcgtat gccgtcttct gcttg                                          265
```

<210> SEQ ID NO 13
<211> LENGTH: 25
<212> TYPE: DNA
<213> ORGANISM: Artificial Sequence
<220> FEATURE:
<223> OTHER INFORMATION: a universal P5 adapter

<400> SEQUENCE: 13

```
aatgatacgg cgaccaccga gatct                                           25
```

<210> SEQ ID NO 14
<211> LENGTH: 24
<212> TYPE: DNA
<213> ORGANISM: Artificial Sequence
<220> FEATURE:
<223> OTHER INFORMATION: an indexed P7 adapter

<400> SEQUENCE: 14

```
caagcagaag acggcatacg agat                                            24
```

<210> SEQ ID NO 15
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID1

<400> SEQUENCE: 15

```
caagcagaag acggcatacg agatatcacg gtgactggag ttcagacgtg tgctcttccg     60

atct                                                                  64
```

<210> SEQ ID NO 16
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID2

<400> SEQUENCE: 16

```
caagcagaag acggcatacg agatcgatgt gtgactggag ttcagacgtg tgctcttccg     60

atct                                                                  64
```

<210> SEQ ID NO 17

<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID3

<400> SEQUENCE: 17
caagcagaag acggcatacg agatttaggc gtgactggag ttcagacgtg tgctcttccg 60
atct 64

<210> SEQ ID NO 18
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID4

<400> SEQUENCE: 18
caagcagaag acggcatacg agattgacca gtgactggag ttcagacgtg tgctcttccg 60
atct 64

<210> SEQ ID NO 19
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID5

<400> SEQUENCE: 19
caagcagaag acggcatacg agatacagtg gtgactggag ttcagacgtg tgctcttccg 60
atct 64

<210> SEQ ID NO 20
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID6

<400> SEQUENCE: 20
caagcagaag acggcatacg agatgccaat gtgactggag ttcagacgtg tgctcttccg 60
atct 64

<210> SEQ ID NO 21
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID7

<400> SEQUENCE: 21
caagcagaag acggcatacg agatcagatc gtgactggag ttcagacgtg tgctcttccg 60
atct 64

<210> SEQ ID NO 22
<211> LENGTH: 64
<212> TYPE: DNA
<213> ORGANISM: Artificial Sequence
<220> FEATURE:

<223> OTHER INFORMATION: sequence of P7 adapter and sample index, P7 adapter R-ID8

<400> SEQUENCE: 22
caagcagaag acggcatacg agatacttga gtgactggag ttcagacgtg tgctcttccg 60
atct 64

<210> SEQ ID NO 23
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID9

<400> SEQUENCE: 23
caagcagaag acggcatacg agatgatcag gtgactggag ttcagacgtg tgctcttccg 60
atct 64

<210> SEQ ID NO 24
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID10

<400> SEQUENCE: 24
caagcagaag acggcatacg agattagctt gtgactggag ttcagacgtg tgctcttccg 60
atct 64

<210> SEQ ID NO 25
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID11

<400> SEQUENCE: 25
caagcagaag acggcatacg agatggctac gtgactggag ttcagacgtg tgctcttccg 60
atct 64

<210> SEQ ID NO 26
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID12

<400> SEQUENCE: 26
caagcagaag acggcatacg agatcttgta gtgactggag ttcagacgtg tgctcttccg 60
atct 64

<210> SEQ ID NO 27
<211> LENGTH: 64
<212> TYPE: DNA
<213> ORGANISM: Artificial Sequence
<220> FEATURE:
<223> OTHER INFORMATION: sequence of P7 adapter and sample index, P7 adapter R-ID13

<400> SEQUENCE: 27

-continued

```
caagcagaag acggcatacg agatagtcaa gtgactggag ttcagacgtg tgctcttccg     60

atct                                                                  64


<210> SEQ ID NO 28
<211> LENGTH: 64
<212> TYPE: DNA
<213> ORGANISM: Artificial Sequence
<220> FEATURE:
<223> OTHER INFORMATION: sequence of P7 adapter and sample index, P7
      adapter R-ID14

<400> SEQUENCE: 28

caagcagaag acggcatacg agatagttcc gtgactggag ttcagacgtg tgctcttccg     60

atct                                                                  64
```